US011093869B2

(12) United States Patent
Sukuta

(10) Patent No.: US 11,093,869 B2
(45) Date of Patent: Aug. 17, 2021

(54) ANALYTICAL SYSTEM WITH ITERATIVE METHOD OF ANALYZING DATA IN WEB-BASED DATA PROCESSOR WITH RESULTS DISPLAY DESIGNED FOR NON-EXPERTS

(71) Applicant: Brewmetrix Inc., Incline Village, NV (US)

(72) Inventor: Sydney Sukuta, Patterson, CA (US)

(73) Assignee: BREWMETRIX INC., Incline Village, NV (US)

( * ) Notice: Subject to any disclaimer, the term of this patent is extended or adjusted under 35 U.S.C. 154(b) by 1024 days.

(21) Appl. No.: 14/622,636

(22) Filed: Feb. 13, 2015

(65) Prior Publication Data

US 2015/0227863 A1 Aug. 13, 2015

Related U.S. Application Data

(60) Provisional application No. 62/092,080, filed on Dec. 15, 2014, provisional application No. 61/939,543, filed on Feb. 13, 2014.

(51) Int. Cl.
*G06Q 10/06* (2012.01)
*G16C 20/70* (2019.01)
(Continued)

(52) U.S. Cl.
CPC ........... *G06Q 10/063* (2013.01); *G16C 20/70* (2019.02); *G16C 20/80* (2019.02); *G16C 20/90* (2019.02)

(58) Field of Classification Search
None
See application file for complete search history.

(56) References Cited

U.S. PATENT DOCUMENTS 4,888,714 A 12/1989 Dingle
5,303,025 A * 4/1994 Fukui ................... G01N 21/718
356/313
(Continued)

FOREIGN PATENT DOCUMENTS

CN 102128794 10/2012
WO 2012160489 A1 11/2012

OTHER PUBLICATIONS

Aeolian Research—Temperate grasslands as a dust source: knowledge, uncertainties, and challenges. M. Shinoda, J. A. Gillies, M. Mikami, Y. Shao.
(Continued)

*Primary Examiner* — Lina M Cordero
(74) *Attorney, Agent, or Firm* — ATIP Law; Ian Burns

(57) ABSTRACT

A method of analysis, analysis system, apparatus, program product and method of supplying analysis of value that incorporates at least one data acquisition device, a central processor which may be located in the cloud with storage capacity and user-friendly interface on any web-enabled device with a communication link between the data acquisition device and the central processor and the central processor and the user interface on a web-enabled device. In the central processor, models of calibration predict values of the properties of interest; a classifier interrogates data to minimize errors in cases that the response variable is non-linear by writing equations to follow each data segment; and a quantifier associates a data class with a specific predetermined calibration model to compute specific parameters of interest. Results of analysis can be determined on the user interface at multiple stages of the analysis.

15 Claims, 32 Drawing Sheets

(51) Int. Cl.
*G16C 20/90* (2019.01)
*G16C 20/80* (2019.01)

(56) References Cited

U.S. PATENT DOCUMENTS

| | | | | |
|---|---|---|---|---|
| 5,351,198 | A * | 9/1994 | Adachi | G01N 21/31 356/319 |
| 5,374,562 | A * | 12/1994 | Simon | C07C 233/25 422/84 |
| 5,790,977 | A | 8/1998 | Kzekiel | |
| 5,991,028 | A | 11/1999 | Cabib et al. | |
| 6,560,546 | B1 * | 5/2003 | Shenk | G01J 3/28 356/302 |
| 6,630,672 | B1 | 10/2003 | Brotherton et al. | |
| 6,737,651 | B1 * | 5/2004 | Lendl | G01N 21/39 250/338.5 |
| 6,751,576 | B2 | 6/2004 | Hall et al. | |
| 6,864,978 | B1 * | 3/2005 | Hazen | A61B 5/0075 356/326 |
| 6,958,479 | B2 | 10/2005 | Burling-Claridge et al. | |
| 6,961,677 | B1 | 11/2005 | Boyswoth | |
| 7,075,064 | B2 | 7/2006 | Oliphant et al. | |
| 7,089,780 | B2 | 8/2006 | Sunshine et al. | |
| 7,194,369 | B2 * | 3/2007 | Lundstedt | G01N 21/274 702/104 |
| 7,333,921 | B2 | 2/2008 | Taylor et al. | |
| 8,880,356 | B2 * | 11/2014 | Corbett | H01J 37/28 250/307 |
| 8,937,282 | B2 * | 1/2015 | Owen | G01N 23/2252 250/306 |
| 9,048,067 | B2 * | 6/2015 | Owen | G01N 23/2252 |
| 9,091,635 | B2 * | 7/2015 | Owen | G01N 23/2252 |
| 2003/0154044 | A1 * | 8/2003 | Lundstedt | G01N 35/00871 702/104 |
| 2004/0000653 | A1 * | 1/2004 | Nordlund | G01N 33/146 250/573 |
| 2005/0266395 | A1 | 12/2005 | Gholap et al. | |
| 2007/0043518 | A1 * | 2/2007 | Nicholson | G16C 20/20 702/23 |
| 2007/0288174 | A1 * | 12/2007 | Young | H01J 49/0036 702/22 |
| 2008/0218733 | A1 * | 9/2008 | Benes | G01J 3/0272 356/51 |
| 2008/0234945 | A1 * | 9/2008 | Walk | G16C 20/20 702/19 |
| 2009/0222390 | A1 * | 9/2009 | Yuta | G06F 17/30412 706/13 |
| 2010/0145896 | A1 * | 6/2010 | Yuta | G06F 19/704 706/12 |
| 2010/0179934 | A1 * | 7/2010 | Howley | G01N 21/359 706/12 |
| 2010/0241598 | A1 * | 9/2010 | Yuta | G06F 19/707 706/12 |
| 2011/0054864 | A1 | 3/2011 | Lundstedt et al. | |
| 2011/0071807 | A1 * | 3/2011 | Hubert | G01N 21/359 703/2 |
| 2012/0116689 | A1 * | 5/2012 | Heinje | G16C 20/80 702/25 |
| 2013/0238252 | A1 * | 9/2013 | Perenon | H01J 49/0018 702/23 |
| 2014/0138537 | A1 * | 5/2014 | Grothe, Jr. | G16C 20/90 250/282 |
| 2015/0036138 | A1 * | 2/2015 | Watson | G01N 21/31 356/402 |
| 2015/0060674 | A1 * | 3/2015 | Levels | G01N 21/3577 250/341.7 |

OTHER PUBLICATIONS

Journal of Chemical Information and Modeling—ChemCalc: A Building Block for Tomorrow's Chemical Infrastructure. Luc Patiny and Alain Borel.

DNA Research—DDBJ Read Annotation Pipeline: A Cloud Computing-Based Pipeline for High-Throughput Analysis of Next-Generation Sequencing Data. Hideki Nagasaki, Takako Mochizuki, Yuichi Kodama, Satoshi Saruhashi, Shota Morizaki, Hideaki Sugawara, Hajime Ohyanagi, Nori Kurata, Kousaku Okubo, Tohihisa Takagi, Eli Kaminuma, Yasukazu Nakamura.

Article Remote Sensing of Environment www.elsevier.com/locate/rse Antonio Plaza.

Article Robust Support Vector Method for Hyperspectral Data Classification and Knoledge Discovery Gustavo Camps.

* cited by examiner

Key: P=parameter

Each parameter or measurement range is a class

| P1 Classes | Classifier Model | Range (a.u.) | P2 Classes | Classifier Model | Range (a.u) |
|---|---|---|---|---|---|
| Class P1.1 | | 1.95 to 2.11 | ClassP2.1 | | 11.23 to 11.76 |
| Class P1.2 | | 2.12 to 2.21 | ClassP2.2 | | 11.77 to 12.24 |
| ClassP1.3 | | 2.22 to 2.27 | ClassP2.3 | | 12.25 to 12.35 |
| Class P1.4 | | 2.28 to 2.36 | ClassP2.4 | | 12.36 to 13.11 |
| Class P1.5 | | 2.37 to 2.67 | ClassP2.5 | | 13.12 to 13.66 |
| ClassP1.6 | | 2.68 to 2.81 | ClassP2.6 | | 13.67 to 13.88 |
| Class P1.7 | | 2.82 to 2.91 | ClassP2.7 | | 13.89 to 14.26 |
| Class P1.8 | | 2.92 to 3.00 | Class P2.8 | | 14.27 to 15.46 |
| Class P1.9 | | 3.01 to 3.08 | ClassP2.9 | | 15.47 to 16.46 |
| Class 1.10 | | 3.09 to 3.12 | Class P2.10 | | 16.47 to 17.29 |

Figure 7.

| P1 CLASSES | CALIBRATION MODEL RANGE (a.u.) | P2 CLASSES | CALIBRATION MODEL RANGE (a.u.) |
|---|---|---|---|
| CLASS P1.1 | 1.95 to 2.11 | CLASS P2.1 | 11.23 to 11.76 |
| CLASS P1.2 | 2.12 to 2.21 | CLASS P2.2 | 11.77 to 12.24 |
| CLASS P1.3 | 2.22 to 2.27 | CLASS P2.3 | 12.25 to 12.35 |
| CLASS P1.4 | 2.28 to 2.36 | CLASS P2.4 | 12.36 to 13.11 |
| CLASS P1.5 | 2.37 to 2.67 | CLASS P2.5 | 13.12 to 13.66 |
| CLASS P1.6 | 2.68 to 2.81 | CLASS P2.6 | 13.67 to 13.88 |
| CLASS P1.7 | 2.82 to 2.91 | CLASS P2.7 | 13.89 to 14.26 |
| CLASS P1.8 | 2.92 to 3.00 | CLASS P2.8 | 14.27 to 15.46 |
| CLASS P1.9 | 3.01 to 3.08 | CLASS P2.9 | 15.47 to 16.46 |
| CLASS 1.10 | 3.09 to 3.12 | CLASS P2.10 | 16.47 to 17.29 |

Figure 9.

Summary of Analytical Regions RMSEP

| Analytical Region | Pre-Outlier RMSEP | Post-Outlier RMSEP |
|---|---|---|
| 1 | .13 | .06 |
| 2 | .09 | .03 |
| 3 | .05 | .05 |
| 4 | .16 | .08 |
| 5 | .06 | .06 |
| 6 | .01 | .01 |
| 7 | .17 | .04 |

Figure 21.

Summary Analytical Classes Cut-off Points

| Analytical Region/Class | Measured Points Min (%) | Measured Points Max (%) | Merged Points Min (%) | Merged Points Max (%) |
|---|---|---|---|---|
| 1 | 11.23 | 12.12 | 11.23 | 12.15 |
| 2 | 12.18 | 12.44 | 12.16 | 12.63 |
| 3 | 12.83 | 13.25 | 12.64 | 13.39 |
| 4 | 13.52 | 14.02 | 13.4 | 14.05 |
| 5 | 14.08 | 15.56 | 14.06 | 15.41 |
| 6 | 15.26 | 16.59 | 15.42 | 16.59 |
| 7 | 16.6 | 17.29 | 16.6 | 17.29 |

Figure 23.

Example of Membership Determination Output

| Sample ID | MS Score | Class 1 | MS Score | Class 2 |
|---|---|---|---|---|
|  | Class 1 | Member | Class 2 | Member 2 |
| BBCP5 | 0.894976 | Yes | 0.105024 | No |
| BBCP6 | 0.85902 | Yes | 0.14098 | No |
| BBKO1 | 1.12553 | Yes | -0.12553 | No |
| BBKO2 | 1.15359 | Yes | -0.15359 | No |
| BBKO3 | 0.9009 | Yes | 0.0991 | No |
| BBKO4 | 0.879891 | Yes | 0.120109 | No |

Figure 24.

| Enter Brew Name: e.g. IPA1 Final Output = EFMA | Range of Expected Results (see Range Table for wort on the next page) |
|---|---|
| 1. Original Extract (%) (PEO) | Allow up to two consecutive ranges to be entered in this column and our system will choose the best analytical region between the two. One entry is mandatory and the second one is optional. |
| 2. Apparent Extract (%) (PEA) | |
| 3. Alcohol (%) *(If wort this option must be grayed out) | |
| 5. Color (EBC) | |
| 6. Bitterness (IBU) | |
| 7. pH (Only available for wort) | |

Figure 29

B. Designated Wort Sugar Extract Ranges

Sugar Extract (PEO/PEA)(%)

| Range/Class | Min | Max |
|---|---|---|
| 1 | 10.95 | 11.67 |
| 2 | 12.06 | 12.38 |
| 3 | 12.4 | 12.64 |
| 4 | 12.64 | 12.9 |
| 5 | 12.91 | 13.13 |
| 6 | 13.14 | 13.39 |
| 7 | 13.39 | 13.7 |
| 8 | 14.44 | 14.64 |
| 9 | 14.65 | 14.86 |
| 10 | 14.86 | 15.16 |
| 11 | 15.32 | 15.76 |
| 12 | 16.19 | 16.88 |
| 13 | 16.76 | 17.09 |
| 14 | 17.34 | 17.84 |
| 15 | 17.91 | 18.72 |

Figure 30

| PFCP 2015_06_16 | Output Range Validation | Recommend Output Range | PREDICT ALL (Overrides all below) |
|---|---|---|---|
| PEO | Pass | Gray-out | predict |
| % Alcohol | Pass | Gray-out | predict |
| Bitterness | Fail | 30 to 40 IBU | Do not predict |
| etc.. | | | |

Figure 31

| Subscriber Company: Company XYZ<br>Brew Stage and Date: PCP mm/dd/yyyy<br>Technician: Ryan<br>Todays Date: mm/dd/yyyy | Output Range | Results |
|---|---|---|
| PEO (-1 Credit) | 10 to 15% | 12% |
| % Alcohol (-1 credit) | 5 to 10% | 8% |
| Bitterness (-1 credit) | 30 to 40 (IBU) | 35 IBU |

Credits used this session:
Total Credits Used: 233
Credits left =267

Would you like to do another test another beer product check-up?
Yes   No

Would you like check-up results sent to the subscriber e-mail account of file?
Yes   No

Figure 32

ANALYTICAL SYSTEM WITH ITERATIVE METHOD OF ANALYZING DATA IN WEB-BASED DATA PROCESSOR WITH RESULTS DISPLAY DESIGNED FOR NON-EXPERTS

CROSS REFERENCE TO RELATED APPLICATIONS

This application claims priority to U.S. provisional patent applications Ser. Nos. 61/939,543, filed Feb. 13, 2014 and 62/092,080 filed Dec. 15, 2014, the contents of each of which are herein incorporated by reference.

FIELD OF THE INVENTION

The present invention relates to analytical systems and in particular to performing analysis of samples across a network.

BACKGROUND

There are many uses for analyzing one or more properties of material. Such analytical systems are commonly considered useful for the agricultural, medical, food and beverage, mining, chemical, and finished hard goods industries, although the analytical systems are not limited to these industries, nor are they limited to industrial use. As one non-limiting example of industrial use, pharmaceutical companies may analyze the concentration of various components of a drug during multiple stages of its production to ensure it meets applicable standards.

Most traditional laboratory tests used to analyze properties of material require 1) a high degree of training and specialization in analytical lab methods, 2) the use of a physical plant, and 3) a significant commitment of funding and time. Non-experts who may want to perform their own tests may then be challenged in cases where they lack the necessary training, funding, and/or locational mobility. Furthermore, users often require multiple machines to test multiple properties of interest of a material in question.

A handful of analytical systems have been proposed—for example, in U.S. Pat. No. 6,560,546 (2003) to Shenk and Westerhaus, U.S. Pat. No. 7,630,848 (2009) to Loosme, U.S. Pat. No. 7,194,369 (2007), and U.S. Pat. No. 8,010,309 (2011) all to Lundstdt et al. In typical systems of prior art, spectrographic instruments located at the site of the material to be tested acquire data which is then transferred to a central processor which may be located within the spectrographic instrument, at the site of the material in question, or at a remote location.

While conventional analytical systems and methods as well as the prior art are generally thought to provide acceptable performance, they also include shortcomings. The prior art generally states that in the data processor, an appropriate calibration model is selected to analyze the data and results are made available thereafter. The prior art neglects to explain, however, the methods by which the appropriate models are selected. In my experience, I have found that more often than not, the majority of real-life data exhibit nonlinear responses. Consequently, without methods to handle nonlinear responses, there are likely to be unacceptable prediction errors and/or samples that do not exhibit a linear response could be declared as outliers. This therefore limits the scope of the prior art to include only sample responses that are perfectly linear.

The prior art also limits user access to the results of the data at the end of one analytical system. In addition, the results of the analysis from existing analytical systems remains inaccessible to non-experts since the systems do not include a user interface that displays results through a modality that non-experts can more easily comprehend.

What is required is an improved system and method for performing analysis.

SUMMARY OF ONE EMBODIMENT OF THE INVENTION

Advantages of One or More Embodiments of the Present Invention

The various embodiments of the present invention may, but do not necessarily, achieve one or more of the following advantages:

the ability to minimize prediction errors, particularly when the response variable exhibits are non-linear;

provide flexibility for the user to retrieve results from any location from which the internet can be accessed;

provide results in a user friendly manner that non-experts can easily understand;

provide users with the option to access results at various stages of the analytical process; and the ability to allow users the flexibility to conduct examinations and to analyze results from a location remote from the substance in question.

These and other advantages may be realized by reference to the remaining portions of the specification, claims, and abstract.

BRIEF DESCRIPTION OF ONE EMBODIMENT OF THE PRESENT INVENTION

In one aspect, there is provided a system or a method for analyzing a product. Data from a product may be obtained by a data acquisition device and transmitted to a data processor. The data processor may perform a classification procedure and a quantification procedure. The classification procedure determines a class for at least one parameter of interest, the class comprising a range of parameter values. The quantification procedure processes the determined class for the at least one parameter of interest and calculates a result value within the range of parameter values for the at least one parameter of interest.

In one aspect, a data processor may perform a classification procedure on a data sample. The classification procedure may comprise executing a universal calibration model that estimates a first class that the data belongs to comprising a first range of parameter values for the at least one parameter and executing a parameter membership classifier model that determines a second class that the sample belongs to, the second class comprising a second range of parameter values for the at least one parameter.

In one aspect, there is provided a system for analyzing a product comprising means for receiving data from a data acquisition device, means for receiving a selection of one or more parameters of interest, means for determining from the data a class for at least one of the parameters of interest, and means for determining a parameter value within the class for the at least one parameter of interest.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

FIG. 7. is a sample library of parameter classifier models;

FIG. 9. is a sample library of quantifications that associates classes with ranges;

FIG. 21 is a summary table of the RMSEP values for the analytical regions prior to and after removing outliers;

FIG. 23 is a table that shows the cut off points for the analytical classes;

FIG. 24 is a table that shows an example of a membership determination output;

FIG. 29 shows a range entry interface for the selected parameters;

FIG. 30 shows example range table for a parameter;

FIG. 31 shows a validation interface; and

FIG. 32 shows a results interface.

DESCRIPTION OF CERTAIN EMBODIMENTS OF THE PRESENT INVENTION

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

Figure 1:
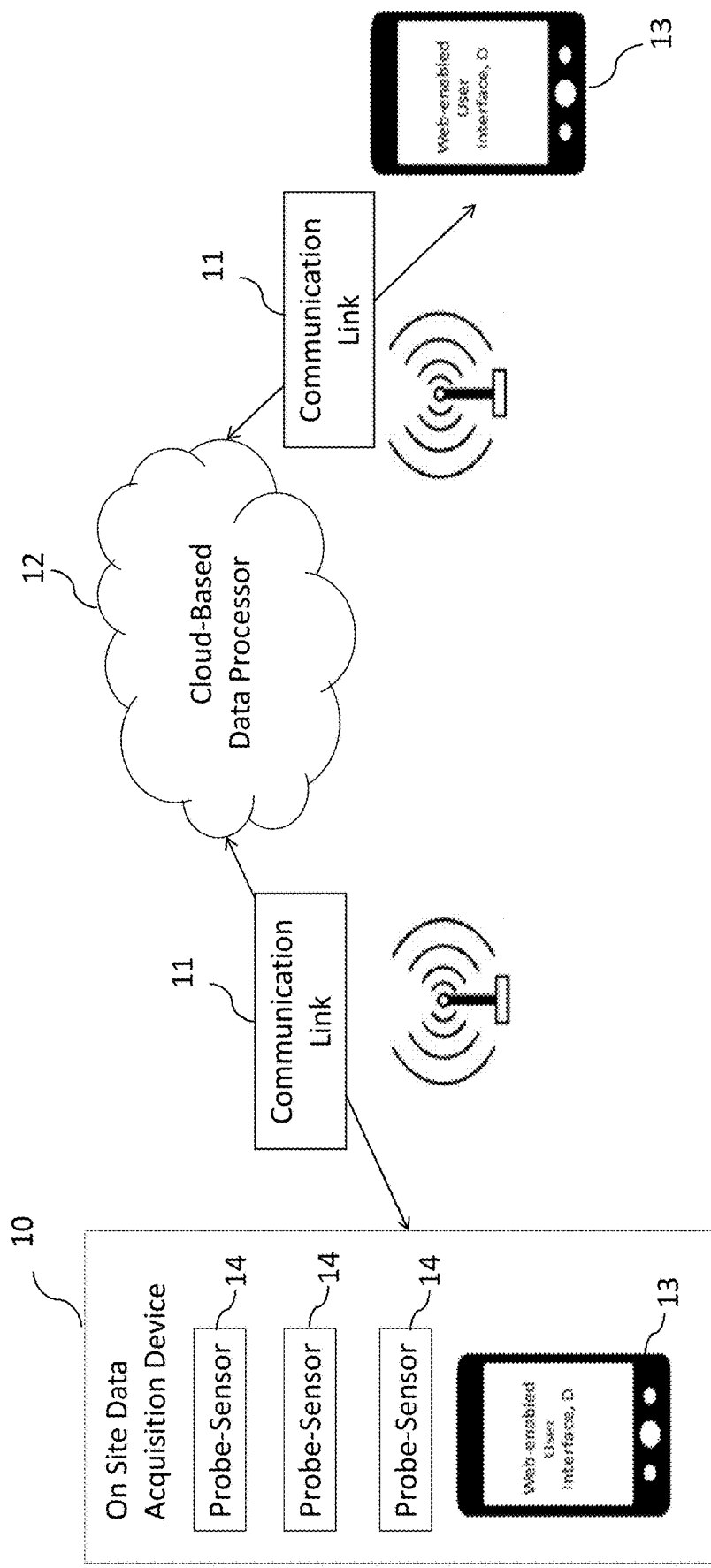
FIG. 1. is a block diagram illustrating the system architecture.

An embodiment of the invention is described with reference to the figures using reference designations as shown in the figures. FIG. 1 shows the system architecture which comprises at least one on site data acquisition device or probe sensor 10 to interrogate the product or substance in question, a cloud-based data processor (data processor) 12 having at least one computer processor to analyze the data and compute results, a web enabled user interface (user interface) 13 to display results on a user computer device in a format that is accessible to non-experts, and in this embodiment two bidirectional communication links 11, one that sends data between the cloud-based data processor 12 and the on site data acquisition device 10 and the other that sends data between the cloud-based data processor 12 and the web-enabled user interface 13.

Figure 2:
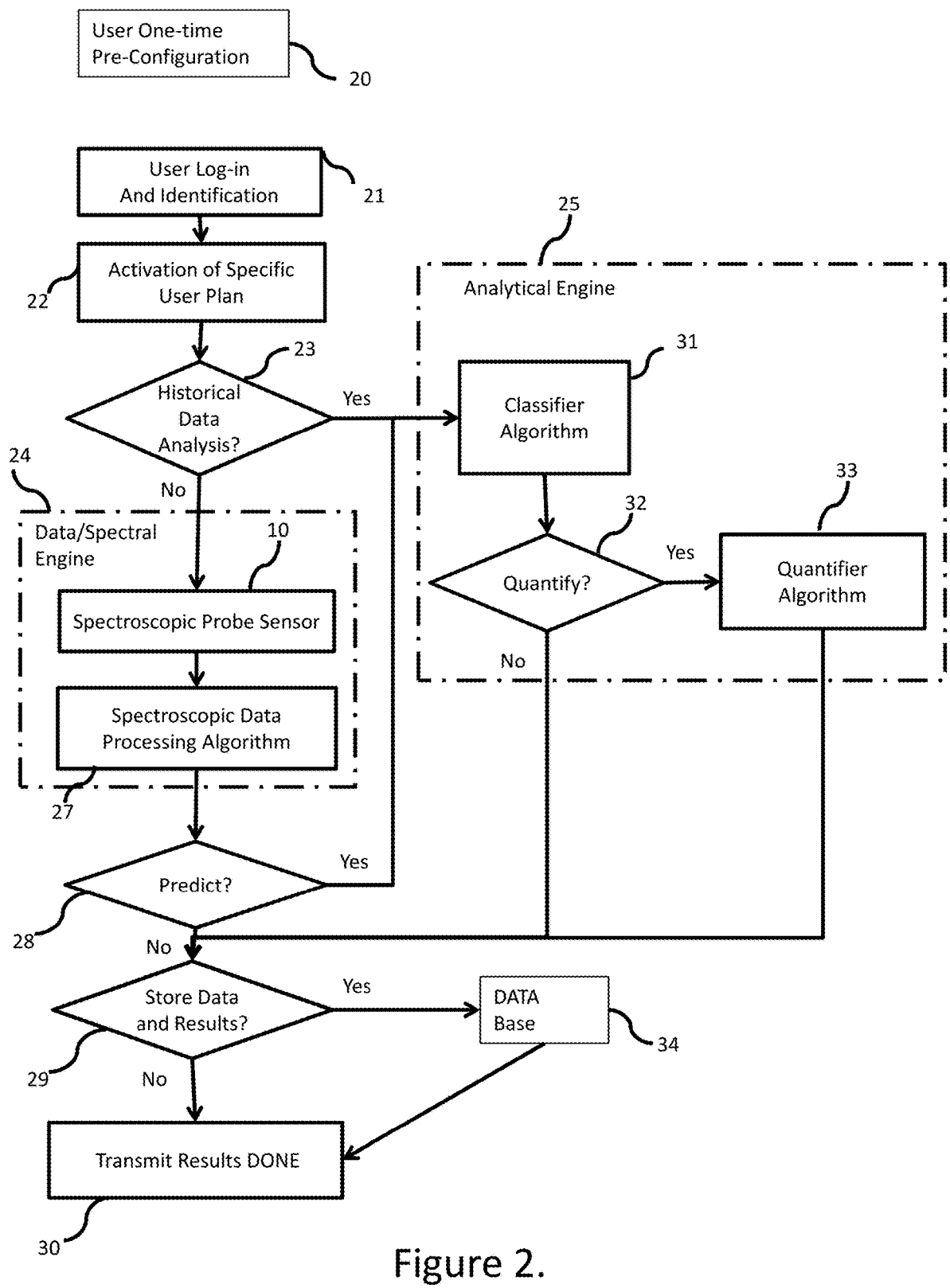
FIG. 2. is a flow chart to establish model feasibility, development, and use.
Figure 3:
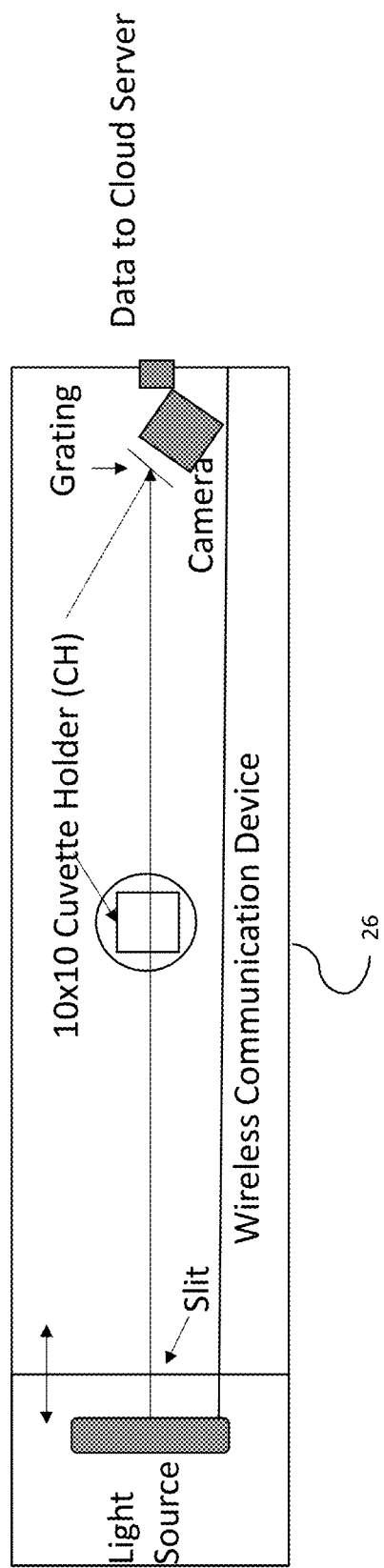
FIG. 3. is an upper perspective view of an example probe-sensor unit.

In this embodiment, the data acquisition device 10 is the apparatus further described in FIG. 3 that collects the data from the substance in question and transfers it to the cloud-based data processor 12 via a communication link 11. In the data processor 12, the data is analyzed as further described in FIGS. 2, 4, 5, and 8. The data is then transferred to a web-based user interface which may be installed on any web enabled device including but not limited to a data acquisition device 10 computer, cellular phone, or tablet. The user interface 13 displays the information in a format that makes the results easy to understand for non-experts.

Bidirectional communication links 11 are responsible for connecting the components 10, 12, 13 in FIG. 1 and can include a plurality of telecommunication modes. Buffering capabilities are stored in the user interface, cloud-based data processor, and data acquisition device to ensure signal integrity and retention in the event that the communication network temporarily fails to transmit signals in real-time.

Figure 10:
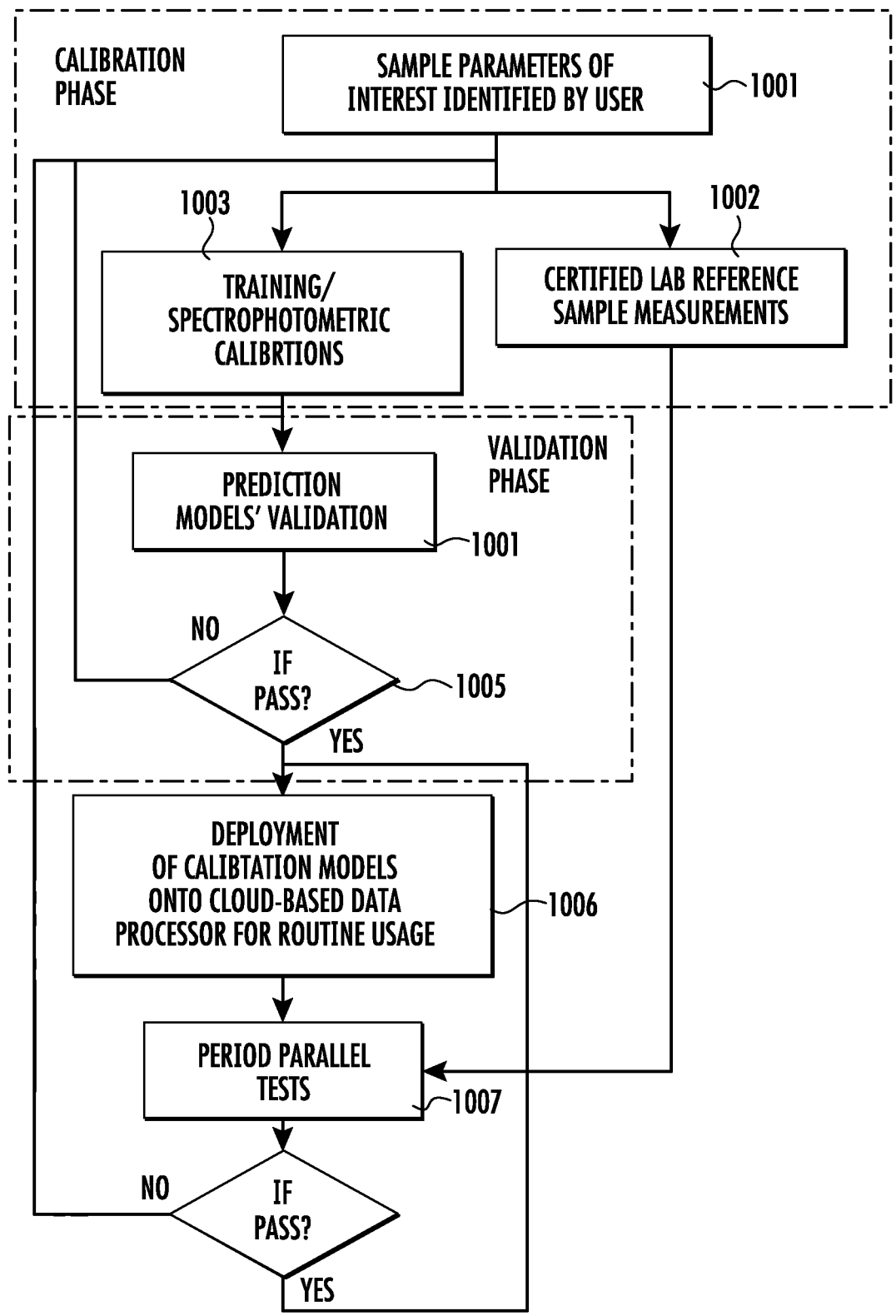
FIG. 10 is a flow chart describing how the sample parameters of interest are determined.

FIG. 10 is a flowchart which demonstrates how the initial parameters of interest for the substance in question are analyzed and applied to the calibration models stored on the cloud-based data processor. The parameters of interest are predefined by the user. For example, if the substance in question is beer, the user may wish to examine a number of parameters, including but not limited to pH, sugar, and alcohol. Once the user pre-selects the parameters of interest 1001, the samples are analyzed in two ways. One is by using a certified lab reference 1002, the other by probing samples from the certified lab in the form of a training set using spectroscopic means 1003. A correlation between the training data set and the certified lab results is identified. A mathematical relationship between the results from the certified lab and the identified spectral points is then developed for the training set. From here, calibration prediction models are used to predict declared parameters from samples other than the training set 1004. If the prediction errors are beyond an acceptable limit (determination 1005), the prediction model is deemed unacceptable and the process begins again from the training/spectrophotometric calibrations and certified lab reference sample measurements. If the prediction model is deemed acceptable, the model is deployed onto the cloud-based data processor 1006. Tests analyzing specified parameters of interest between a certified lab and the prediction model used in the cloud-based data processor are parallel tested periodically 1007 to ensure there are no drifts. In cases where a periodic test fails, the associated prediction model is sent back to the Training/Spectrophotometric Calibrations step of the process.

FIG. 2 is a flowchart which demonstrates the feasibility of the invention. The process shows the way the data is obtained, computed, stored, and displayed, as well as how the user interacts with the system. During the initial use as shown in block 20, the system undergoes a one-time pre-configuration completed by the user using the web-enabled user interface 11.

During all subsequent uses, the system is initiated through block 21, a user log-in and identification. One object of block 21 is to retrieve historical data and present analytical options specific to the user. Thus the successful application of block 21 automates the activation of block 22 which retrieves the specific user plan. Then, in block 23, the user is given an option to either select data previously collected, or to collect new data to be analyzed.

Figure 4:
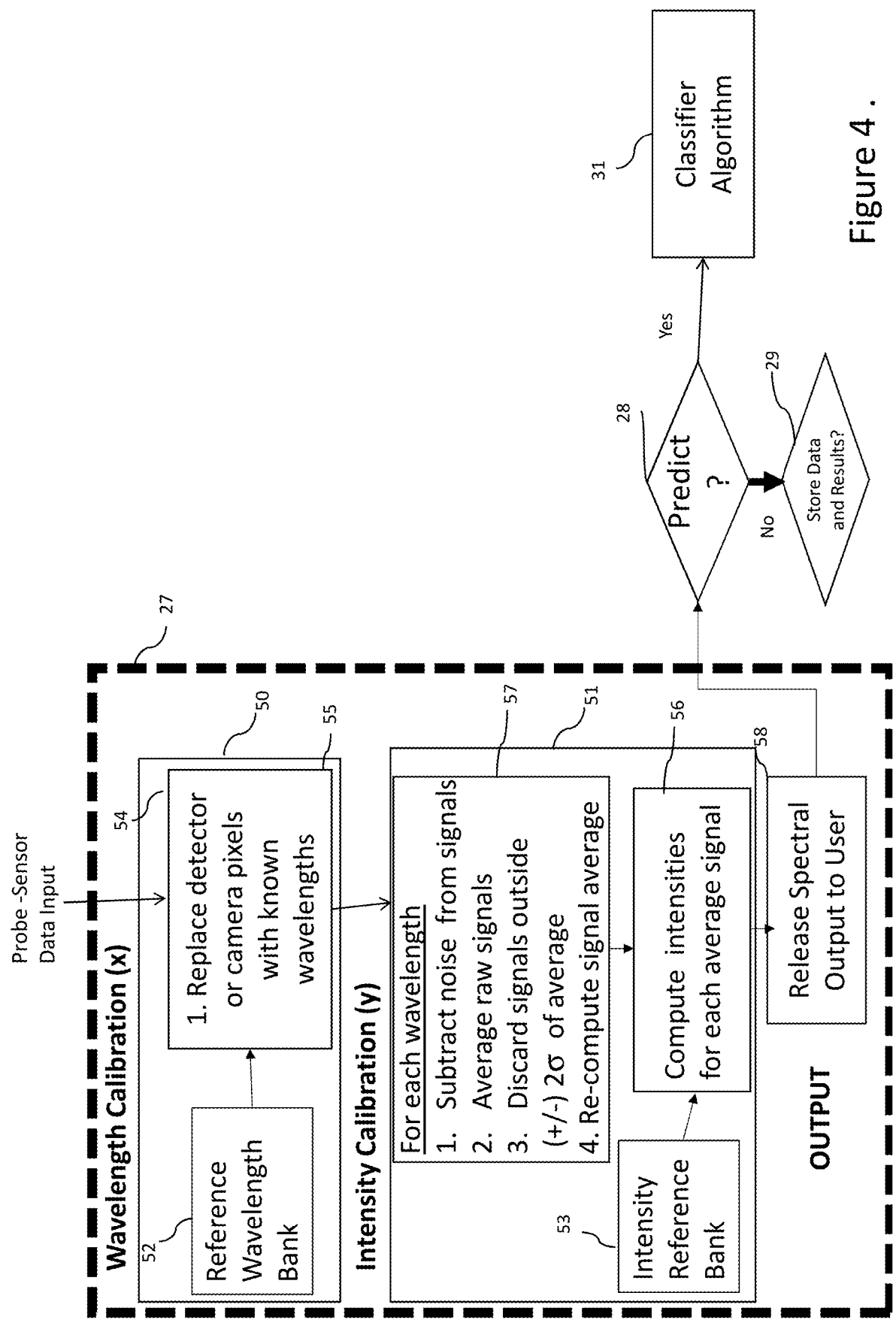
FIG. 4. is a flow chart demonstrating development and use of a Data/Spectral Engine.

In cases when historical data analysis is not selected, the spectroscopic probe sensor 10 is employed to collect data from the substance in question and transfers that data using a communication link 11 to the cloud-based data processor 12 where the data is analyzed using a spectroscopic data processing algorithm 27 as shown in the data/spectral engine 24 and further described in FIG. 4. Once analyzed in Block 27, control goes back to block 28. Depending on the user preferences selected at the time of system configuration, results are either displayed on the user interface 13 or the data is sent to the classifier algorithm 31 in the analytical engine 25 to undergo further analysis.

The analytical engine 25 includes two algorithms: the classifier algorithm 31 and the quantifier algorithm 33. The object of the classifier algorithm 31 is to approximate the ranges of the sample properties of interest i.e. parameters characterizing the sample. After data passes through block 31, it either transfers to the quantifier algorithm 33 to undergo further analysis, or the results are displayed, pending user preferences at the time of system configuration. The classifier algorithm 31 is further detailed in FIG. 5. In cases where the sample data transfers to the quantifier algorithm 33, it undergoes further interrogation to precisely predict values for the sample properties of interest i.e. parameters characterizing the sample. The quantifier algorithm is further detailed in FIG. 8. Once the data in block 33 has been analyzed, it transfers to block 29 where the results may be stored in a database prior to displaying on the web-enabled user interface 13. Alternatively, results may directly transmit to the user interface 13 or any other web-enabled device of choice. Once results are transmitted in block 30, the process has finished.

Figure 11:
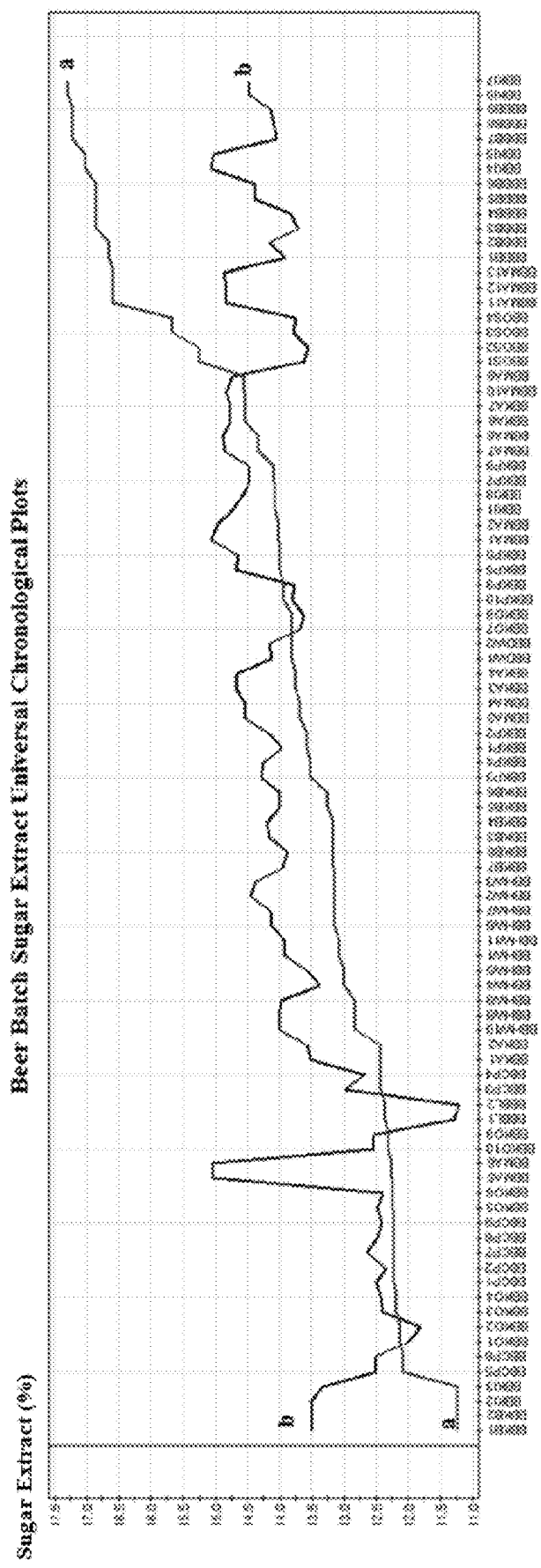
FIG. 11 is a graph depicting both standard reference model results plotted against Universal Calibration Model results which were taken from actual samples of sugar content measured from a beer batch.

The example in FIG. 11 shows how this analytical system improves accuracy of results when compared to conventional methods. This example shows the results from a test of original sugar percent of a beer batch in production. The data in this figure show the results of a Partial Least Squares (PLS) universal calibration model which is referred to as the "Chronological Plot." The horizontal axis represents the different samples analyzed while the vertical axis represents the measurements of the samples' sugar extract. Line "A" represents the results measured from using standard reference methods.

Line "B" represents the output of the universal calibration model (UCM) developed using the reference method results and the spectral data for each sample. Ideally, Line B would track and overlap Line A very closely. However, because Line B is not similar to Line A, it is apparent that applying only the data results from the UCM to a sample parameter of interest, as per the prior art, does not produce the greatest accuracy. This figure demonstrates that the examples from prior art are limited to linear data.

FIG. 3 is a block diagram of a basic probe sensor data acquisition device 10, which may be used to collect sample data from a product or substance in question. This device is considered generic and operates by shooting light onto the substance in question, thereby collecting pixels and signals to obtain a spectrographic sample. Other types of samples and sample collection devices will be apparent to the person skilled in the art. The probe sensor used in this analytical system transfers the data collected to a web-based server through any type of wireless connection device, including but not limited to Wi-Fi, Bluetooth, and cellular radio.

In FIG. 4, the sample data transmitted from the data acquisition device 10 is transferred into the data/spectral engine 27 where the signals received are converted to a suitable data format. The data/spectral engine 27 is located in the data processor instead of the probe sensor. In block 50, a wavelength (x-axis) is assigned based on the average of the pixel readings and is calibrated using a reference wavelength bank 52. Then in block 51, the appropriate intensities for the sample reading are assigned. To initiate this process in block 57, the system subtracts noise from each wavelength signal. The raw signals are then averaged. After this step, any signals that fall within +/− two standard deviations outside of the mean are discarded and the remaining signals are then averaged again. At this stage, the final average for each signal is computed using the intensity reference bank 53 to assign the accurate intensity for the signal. The data is then released to the user through block 58. In block 28, the data either transfers to the classifier algorithm 31 to undergo further analysis, or it displays the results with the option to store them in block 29, depending on the user specifications.

Figure 5:
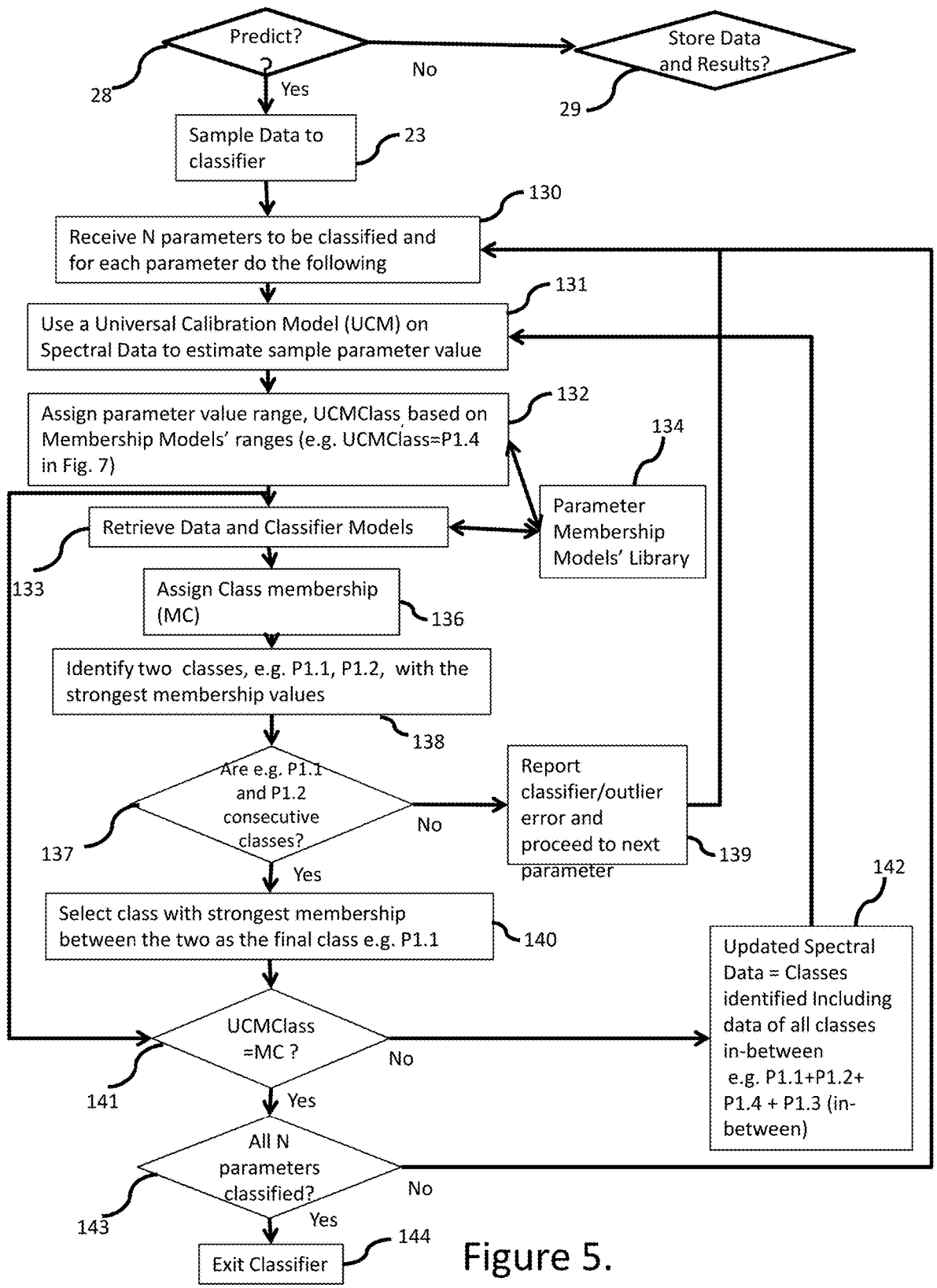
FIG. 5. is a flow chart describing the development and use of a Classifier Algorithm.
Figure 6:
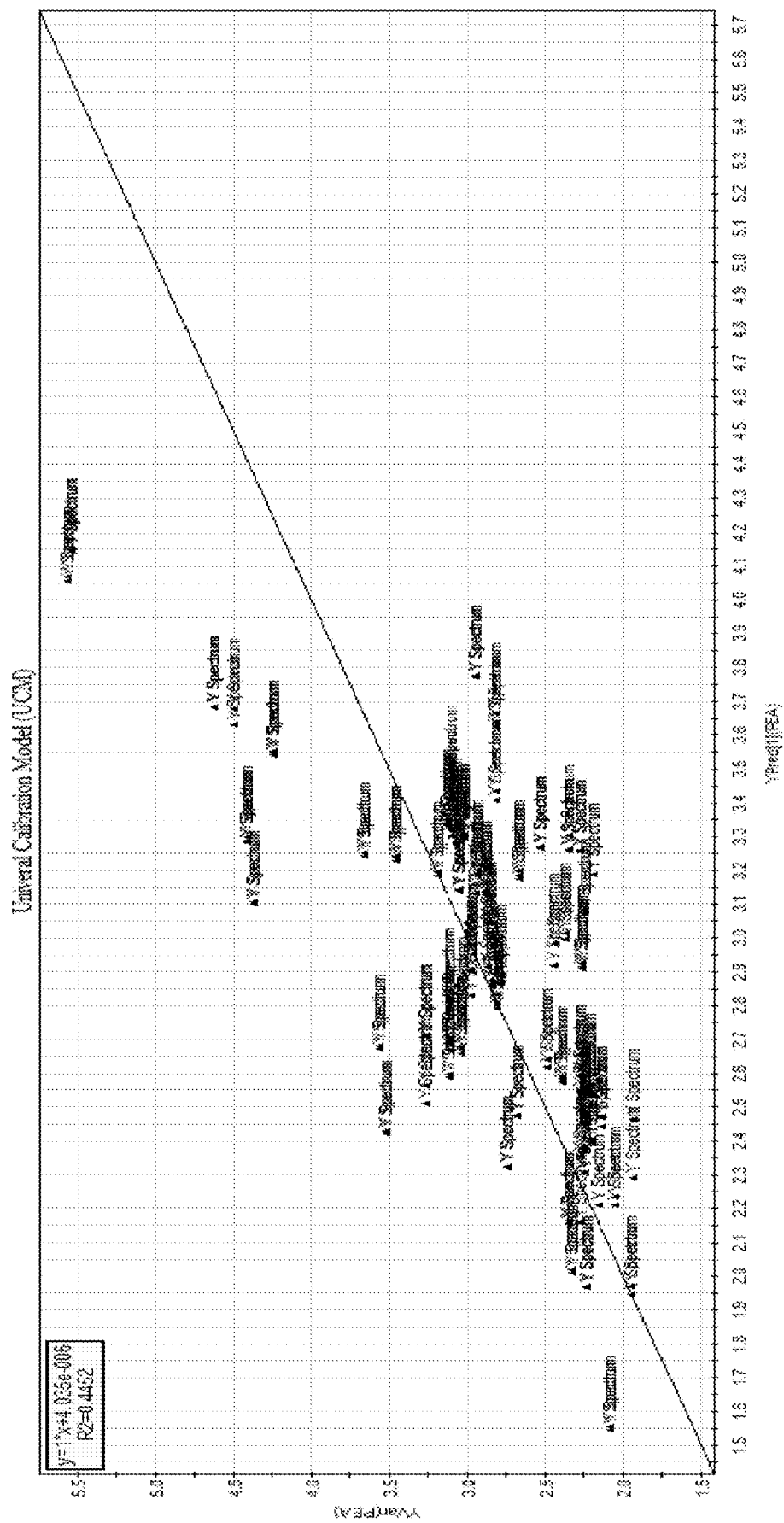
FIG. 6. is a prediction versus observed graph showing results of nonlinear data derived from samples of beer.

FIG. 5 demonstrates how samples that enter the classifier algorithm 31 are computed and analyzed. The classifier algorithm is responsible for determining results of the highest degree of accuracy possible, particularly when examining nonlinear data. In block 23, the sample data are transferred into the classifier and then assigned a predetermined number of parameters. Using the above example, if the substance in question is beer, the parameters assigned may include but are not limited to pH, sugar, or alcohol content. Once parameters have been assigned, the data proceeds to block 131 where it is interrogated by a universal calibration model (UCM), crude classifier to compute a crude estimate for the value of each sample parameter. As an example, FIG. 6 shows the results from a UCM of a sample of beer plotted on a graph. Once the UCM 131 is finished, block 132 assigns a range of membership models to the sample data. The range is based on predetermined membership models ranges. FIG. 7 highlights one example of a predetermined membership model reference library. In FIG. 7, a P refers to each parameter or measurement range which is a class.

The sample parameter value determined using the UCM, block 131, and its assigned parameter value range are transferred to and stored in block 141 as the sample data continues to block 133 to be analyzed using the Parameter Membership Classifier Model (PMM). In block 133, the sample data is retrieved along with the parameter membership models library. Using the Parameter Membership Models' Library 134, the data is assigned a class membership in block 136. To achieve this, the system first splits the parameter classes in half between a Class Range A and Class Range B. Then the membership algorithm (PMM) is run to determine which half the sample parameter belongs to. If the PMM identifies the Class Range A as the membership of the parameter, then the parameter classes in Class Range A are split in half again into Class Range A1 and Class Range A2. Again, the membership algorithm is run, and this pattern continues until there are no more class memberships to split in half.

In block 140, the system selects the class with the strongest membership from blocks 138 and 137 and proceeds with this class as the final. The final class is transferred to Block 141 where it is compared against the results from the universal calibration model, which had been stored in block 141 earlier. If the two classes (the universal class and the membership class) are equal, the system recognizes that the desired level of accuracy has been reached and proceeds to block 143. If the two classes are not equal, the data is directed back to the crude classifier 131 to be computed again.

However, before the data reaches block 131, it must pass through block 142 where the system discards all of the data that exists outside of the range identified between the crude classifier 131 and the membership classifier 136. For example, consider the sample of beer in FIG. 6 and imagine the crude classifier 131 estimates its value on the x-axis as 4.0 while the membership classifier 136 estimates it at 4.4. In this case, the system would dispose of all the data points less than 4.0 and greater than 4.4 before proceeding with the cycle again starting with block 131. This cycle is repeated in the classifier until the point that the data from the UCM 131 and the Membership classifier 136 matches in block 141. Once the data matches, the system checks to see if all of the sample parameters have been classified. If so, the data exits the classifier 144. If not, the system begins again at block 130 where it identifies the parameter(s) that remains to be classified.

There are several other parameter classification algorithms that can be applied during the classifying stage. The PMM classification scheme is suitable for multiple classes, but in some examples and practical application, it may be preferable to work with two samples at a time. As the algorithm narrows down the class ranges, it is able to improve accuracy at capturing the results from nonlinear data. This is in comparison to the prior art which typically only applies a UCM calculation (crude estimate) to arrive at the final result.

Figure 8:
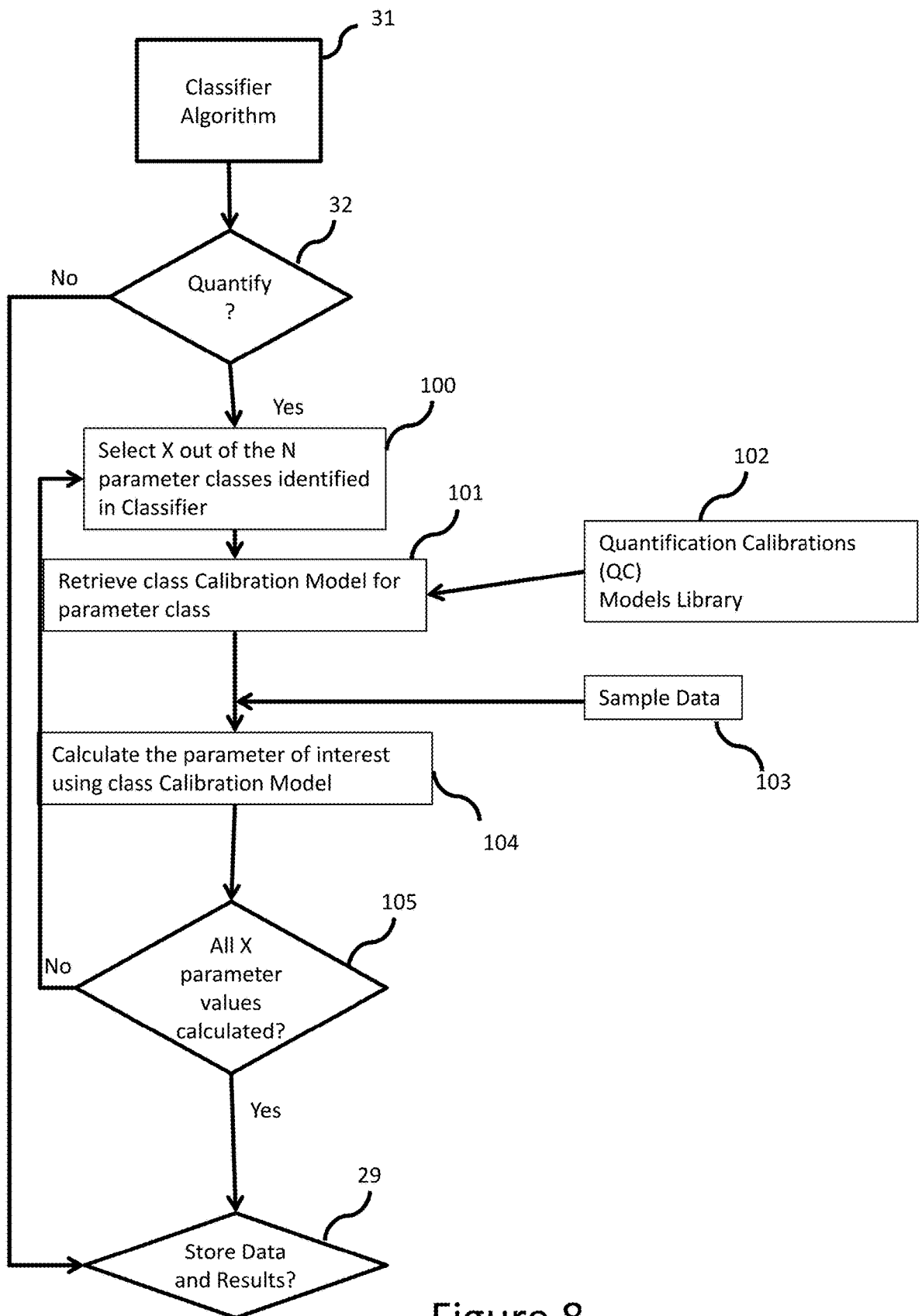
FIG. 8. is a flow chart describing the development and use of a Quantifier Algorithm.

After the classifier has determined the classes for all parameters of the sample in question, the system initiates the quantifier algorithm 33, shown in FIG. 8. The objective of the quantifier 33 is to calculate the precise value of each parameter in question based on the narrow range provided in the classifier 31.

In cases where the user programs the system to display results after the classifier, block 32 will automatically send the data to block 29 where results are either stored and displayed or immediately displayed depending on the user's pre-programmed preferences. In cases where the user chooses to run the sample through the quantifier, block 32 automates the initiation of block 100 where the system identifies all parameters that were analyzed in the classifier 31 and automates the quantifier 33 to quantify a final value for each of the parameters in question. Like the classifier in FIG. 5, the quantifier deals with each parameter sequentially. In block 101, the quantifier retrieves the appropriate equations for the parameter class by referencing the Quantifications Calibration Models Library 102. The system then receives the sample data 103, and calculates the parameter of interest value using the appropriate class calibration model in block 104. FIG. 9 shows an example of the Quantifications Library that associates classes with ranges. In FIG. 9, each P refers to a parameter or measurement range which is a class. Once the value is calculated, the system checks in block 105 if all of the parameters from the classifier 31 have been quantified. If not, the system initiates again in block 100 to select a remaining parameter, and will run through this cycle (block 100-105) until all parameters are quantified. Once quantified, the data results proceed to block 29 where the system computes whether to store the data or immediately display results depending on the user preference.

Figure 12:
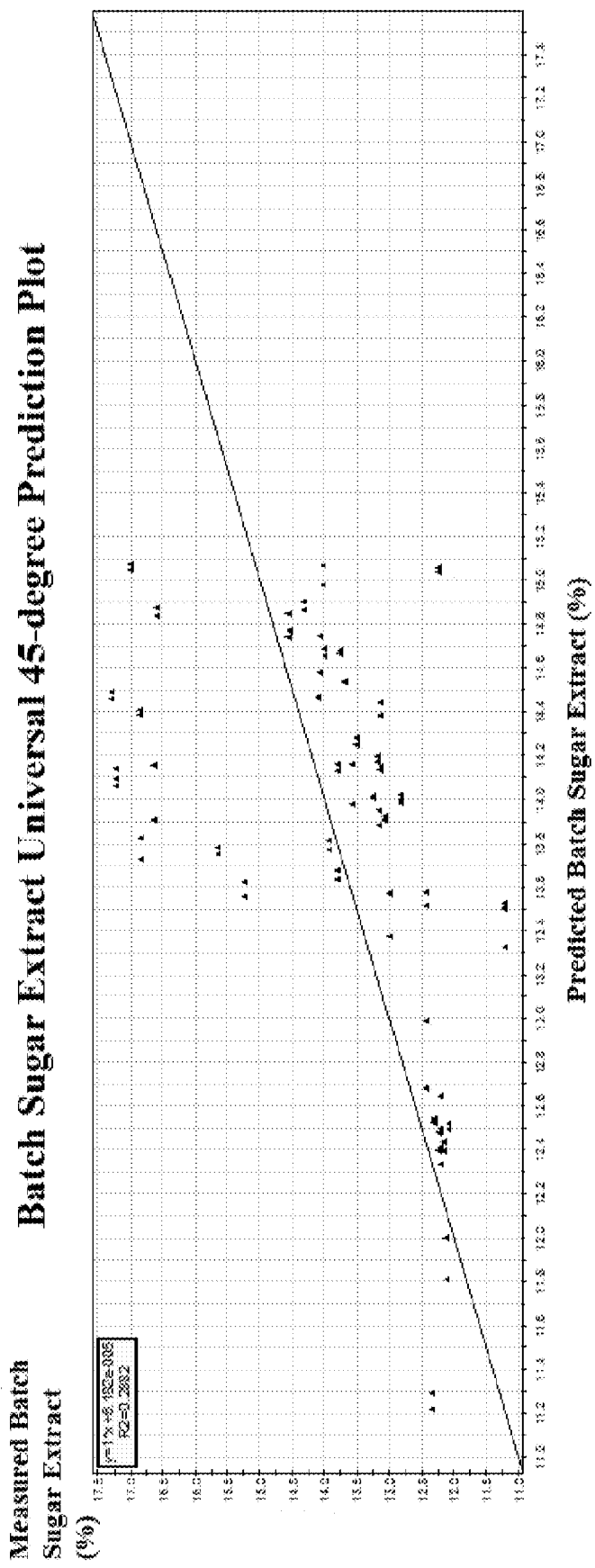
FIG. 12 is a 45 degree prediction plot graph that shows the actual measurements of sugar content from beer batches plotted against the predicted 45 degree line.
Figure 13:
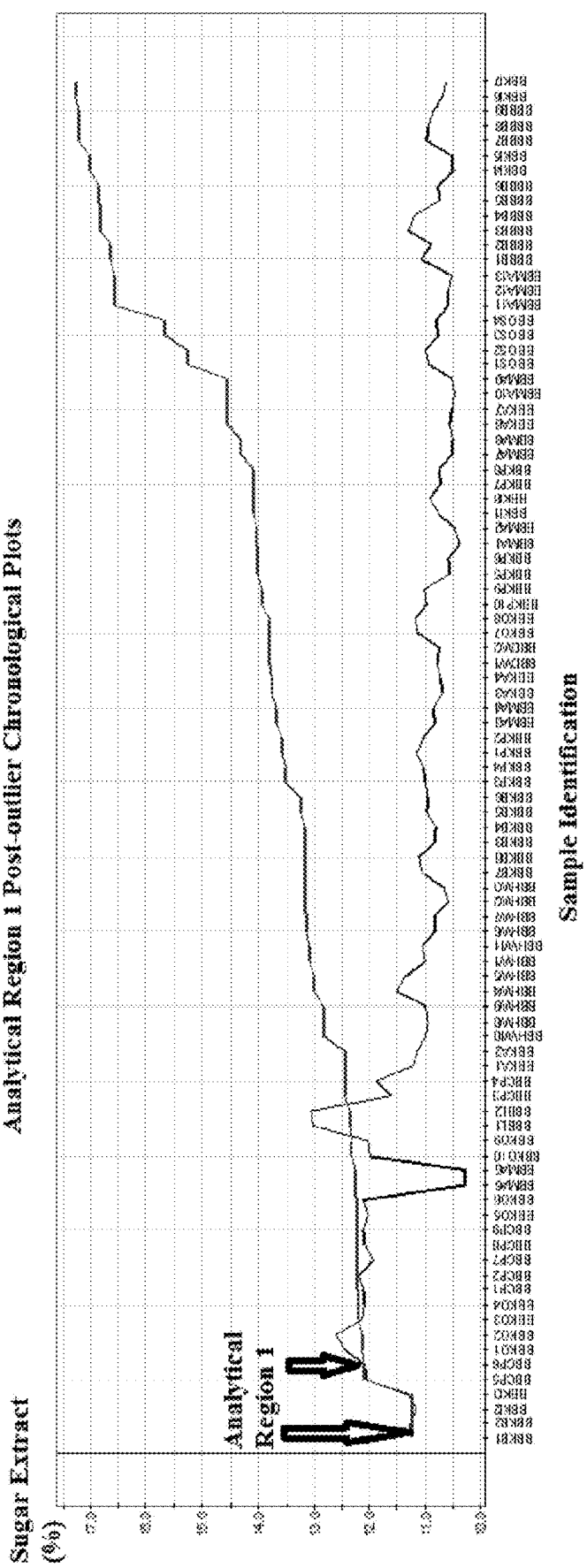
FIGS. 13-19 show actual examples of analytical regions of chronological plots examining sugar content in a batch of beer after eliminating outlier data.
Figure 14:
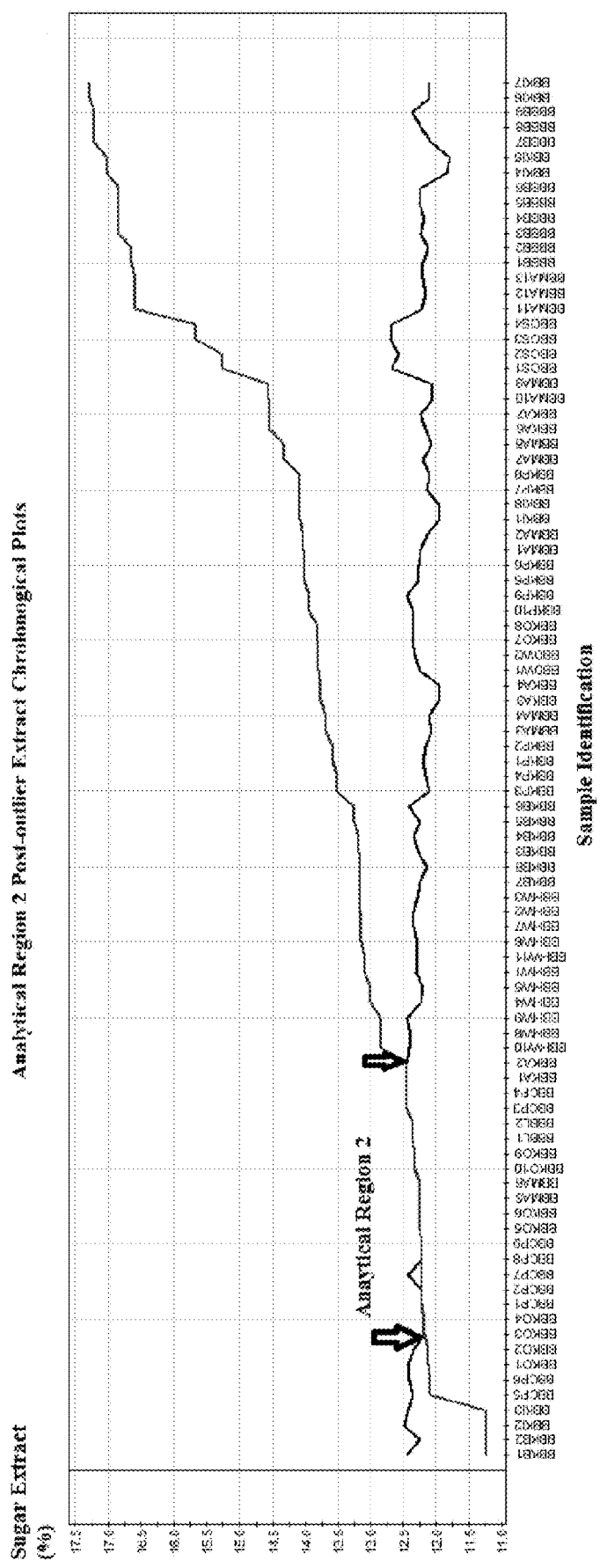
Figure 15:
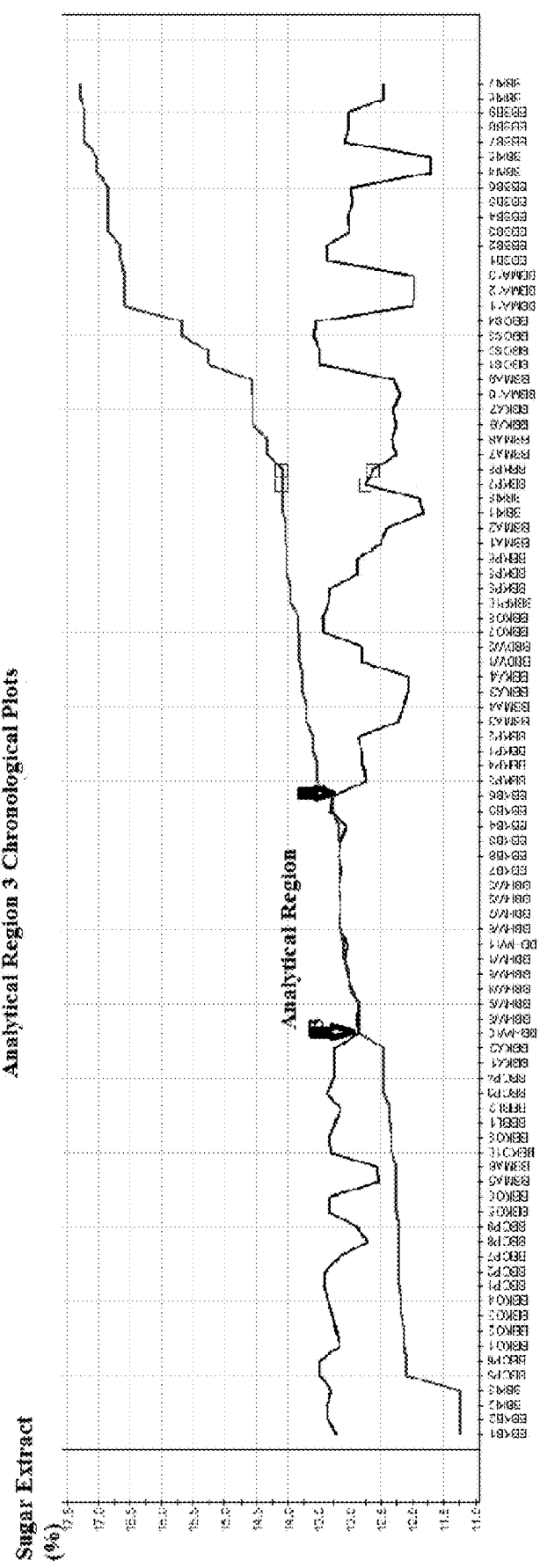
Figure 16:
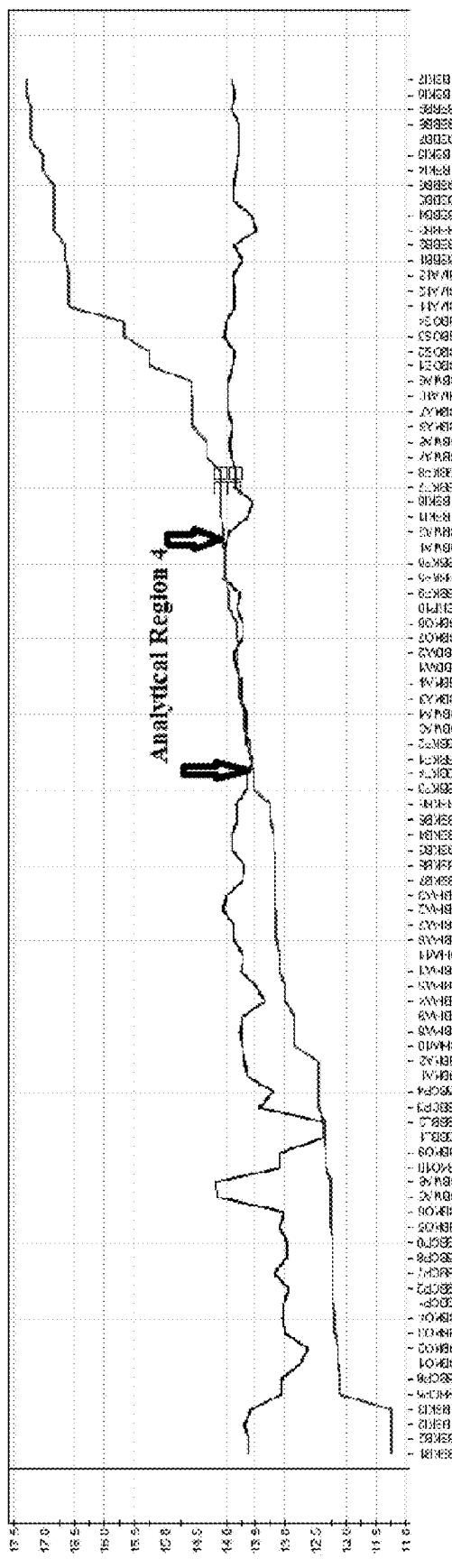
Figure 17:
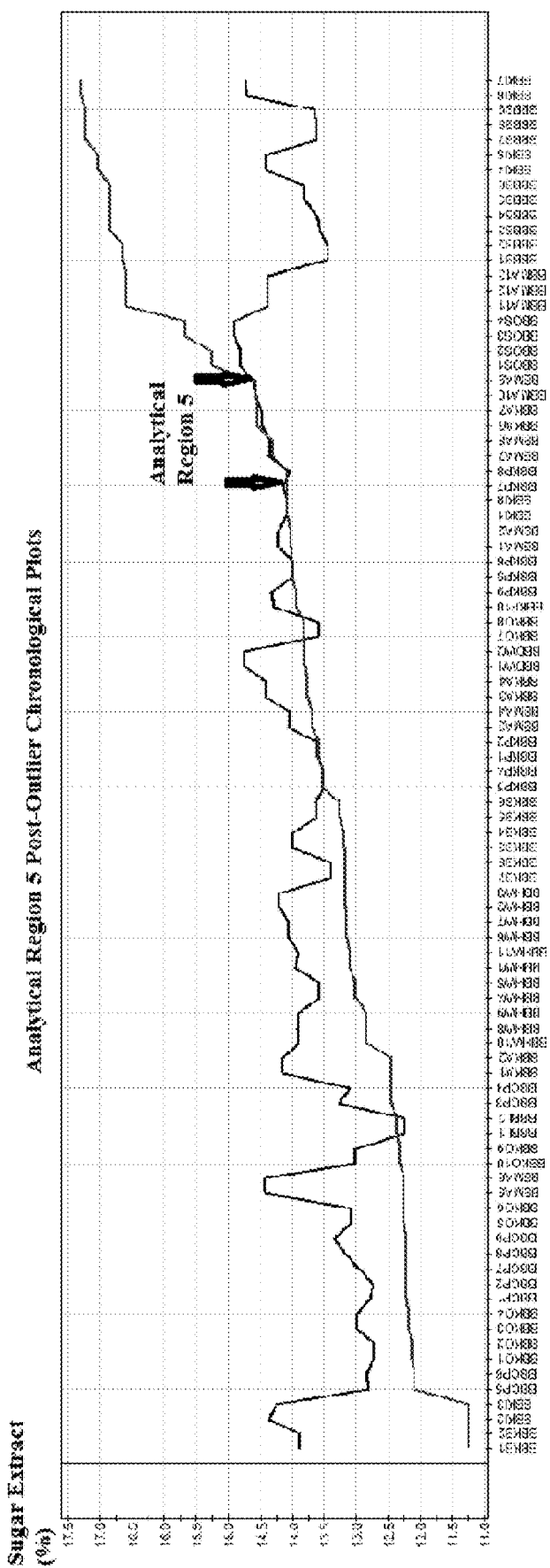
Figure 18:
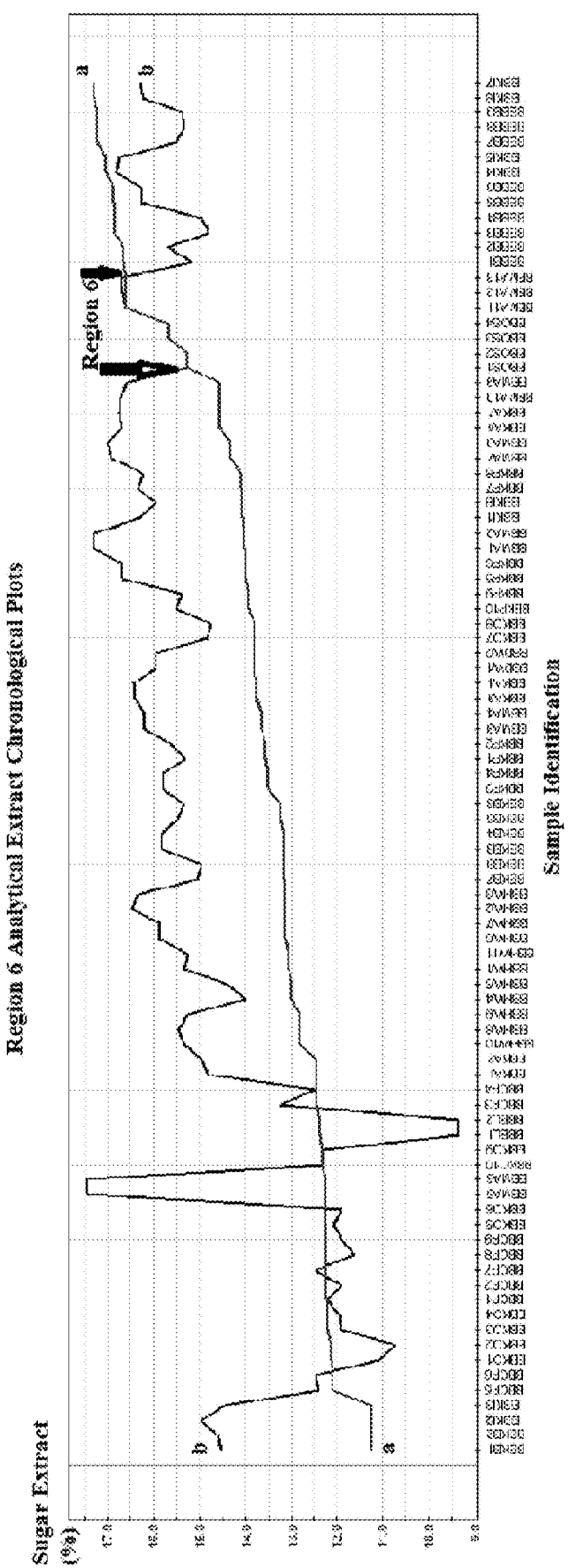
Figure 19:
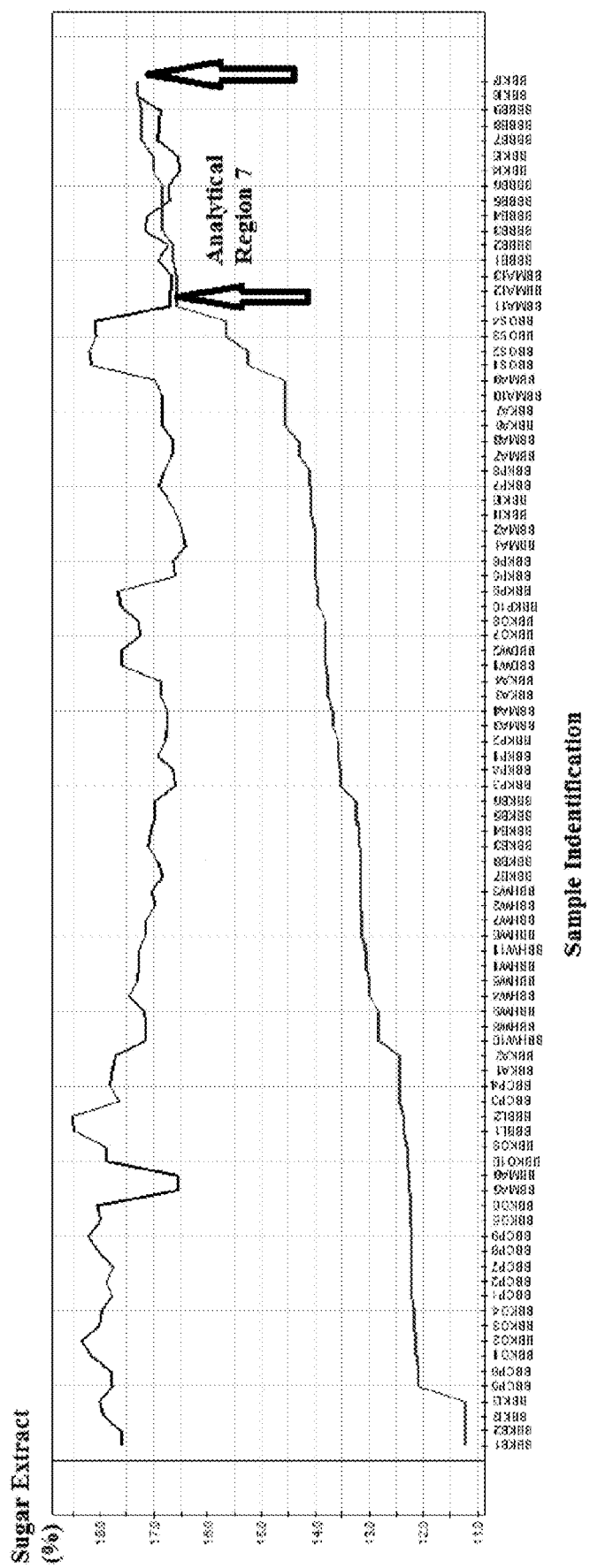

Having described the process of the analytical system, there will be described the numerical diagnostic features used in assessing the quality of our calibration and prediction models. FIG. 12 shows a 45 degree prediction plot where the geometrical shapes within the graphical plot represent the different samples analyzed.

Ideally all the samples should lie along the 45-degree line indicating a match between the reference method measured and predicted results. This may be referred to as the "45-degree Cluster Rule," which is fairly qualitative but the numerical diagnostic feature associated with it is the Root-mean-Square Error of Prediction (RMSEP) discussed below:

$$RMSEP = \Sigma(Measured - Predicted)2/N$$

Where N is the number of sample readings.

For best prediction results from a model, as a rule of thumb, it is desirable to have a calibration and prediction model that results in the least significant digit (LSD) of the reference results overlapping with the most significant digit of the RMSEP, which shall be referred to as the "LSD Error Rule." For example if a measured value is 12.09, then an RMSEP of 0.11 will yield a LSD error violation while a RMSEP of 0.01 will not.

In FIG. 12, the horizontal axis represents the predicted values and the vertical axis represents the measured percent sugar extract. In the specific example, the test is Sugar Extract percentage. The triangular dots in the graph represent the different samples analyzed. Ideally all the samples should lie along the 45-degree line indicating a match between the reference method measurements and the predicted results. For the best prediction results from a model, it is an aim to have a calibration and prediction model that results in the least significant digit (LSD) of the reference results overlapping with the most significant digit of the RMSEP. This "LSD Error Rule" is persistently violated as long as there are outliers in the data set although there are a few occasions where it may be mildly violated after all outliers have been removed. The universal calibration model has a Root-mean-Square Error of Prediction (RMSEP) of 1.45 for sugar percent extract and this violates the LSD Error Rule since the measured results have their least significant digits in the hundredths place.

Figure 20:
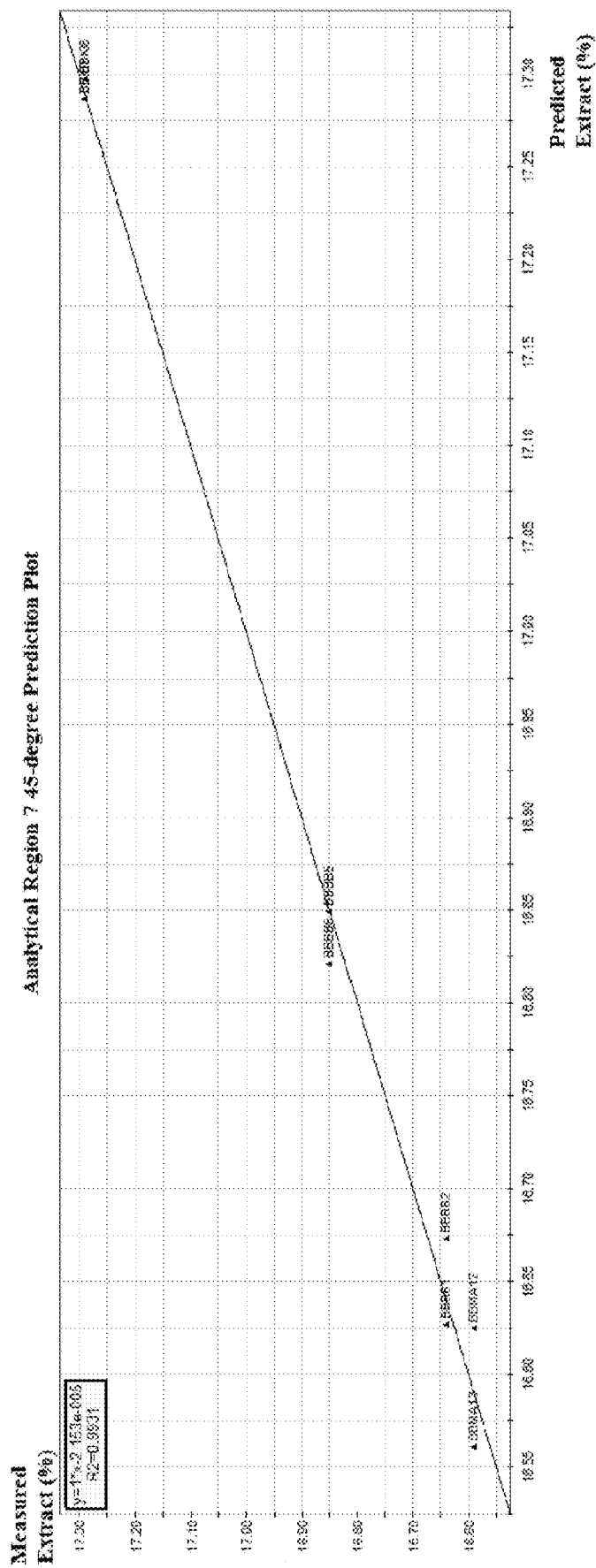
FIG. 20 is a 45 degree prediction plot graph for analytical region 7.

To improve the prediction results, the analytical system in question employs the classifier and quantifier algorithms, which segment the chronologically ordered data into linear and "quasi" linear sections and repeat the same analysis on these localized analytical regions. In this particular sugar extract example seven regions were identified. FIGS. 13 to 19 show the analytical regions 1 to 7 Chronological Plots, after eliminating outlier data using appropriate methods where applicable. FIG. 20 shows that by breaking the range down into analytical regions, the sample data more closely follows the 45 degree line for that region (analytical region 7 shown).

Figure 22:
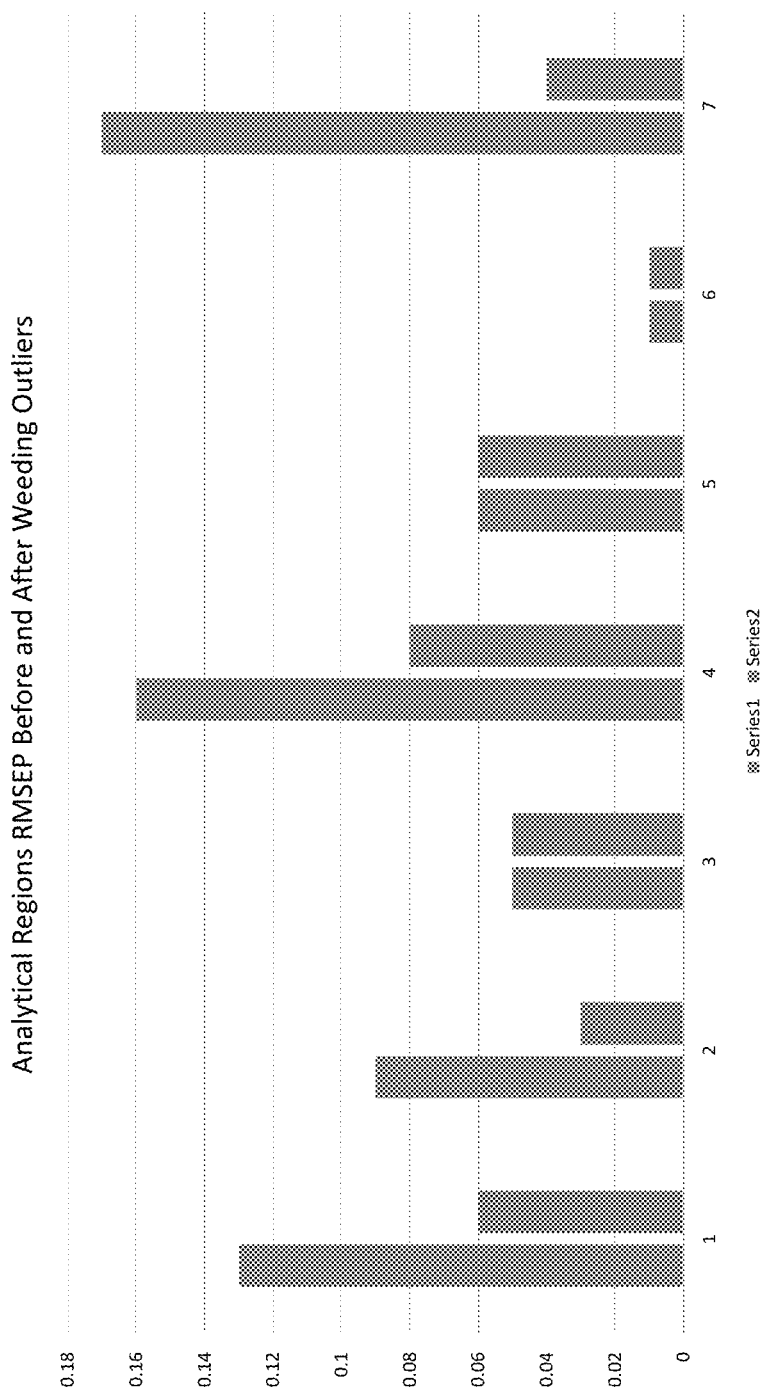
FIG. 22 is a graph representation of the data of FIG. 21.

FIG. 21 shows a summary table while FIG. 22 shows a graph that both demonstrate the RMSEP values of the seven analytical regions before (series 1) and after (series 2) the outliers have been removed. FIGS. 21 and 22 show that for four of the seven regions, the RMSEP values have been reduced significantly, thereby demonstrating that the outlier removal process can greatly improve the results.

A newly scanned or stored sample spectral data set is routed to the Classifier where the associated UCM interrogates it to ascertain the value of the parameter of interest. The determined parameter value is used to identify an analytical class of the sample.

Class discriminant equations are developed such that they assign numerical values expressing the probability of membership in the classes being tested for or neither. The discriminate equations use pre-selected wavelengths' output intensities, $\lambda_1$, $\lambda_2$ etc., and pre-assigned coefficients associated with each of the selected wavelengths, $a_1$, $a_2$ etc.

Let $c_0$ be a pre-determined constant associated with a class discriminant equation Member Score=$c_0+a_1\lambda_1+a_2\lambda_2+\ldots$ For example:

| Member If | Borderline Member If | Not a Member |
|---|---|---|
| Member Score (MS =) .65 <= MS <= 1.35 | .35 < MS < .65 | MS > 1.35, MS < .35 |

FIG. 24 demonstrates an example of the membership determination output that is based on the analytical class cut off points of FIG. 23.

The Quantifier will precisely predict the parameter value (PV) of interest of a sample by evaluating the equation that utilizes the spectral intensity output from pre-selected wavelengths as shown below.

PV=$b_0+o_1\lambda_1+o_2\lambda_2+\ldots$ where
$b_0$ is a pre-determined constant
$\lambda_s$ are pre-determined wavelengths, and
$o_1$ are the spectral intensities at the preselected wavelengths.

The prediction equations stored in the library will have the format shown above, even though some of them may have higher order terms such as quadratic, cubic etc. For example if the equation for % Alcohol has:

$b_0=3$ $o_1=5$ $o_2=6$ then

% Alcohol=$3+5\lambda_1+6\lambda_2$

When a sample is spectroscopically scanned the system will retrieve the intensities associated with wavelengths $\lambda_1$, e.g. 550 nm, and $\lambda_2$, e.g. 622 nm, and input, and evaluate the parameter, e.g. % Alcohol, from these measurements.

A specific embodiment of the invention will now be described with reference to FIGS. 25 to 32 and to a beer brewing application, though the person skilled in the art will readily understand that the methods and interfaces described can be applied to many different applications, including standardized and non-standardized processes. A standardized process is considered to be a process that follows a well established series of process steps, though variations within these process steps may be possible.

A user may pre-register for an account with an online analysis lab. The user may enter into a payment plan with the online analysis lab. For example, the user may pay a fixed amount per month or may pay on a per-use or other basis. The user's payment may entitle the user to a number of analysis services, a period of analysis services, or a combination. Specific registration and payment plans are not considered pertinent to the present invention and with online registration systems being well established for many internet based services, no further description of the registration process is considered necessary herein.

Figure 25:
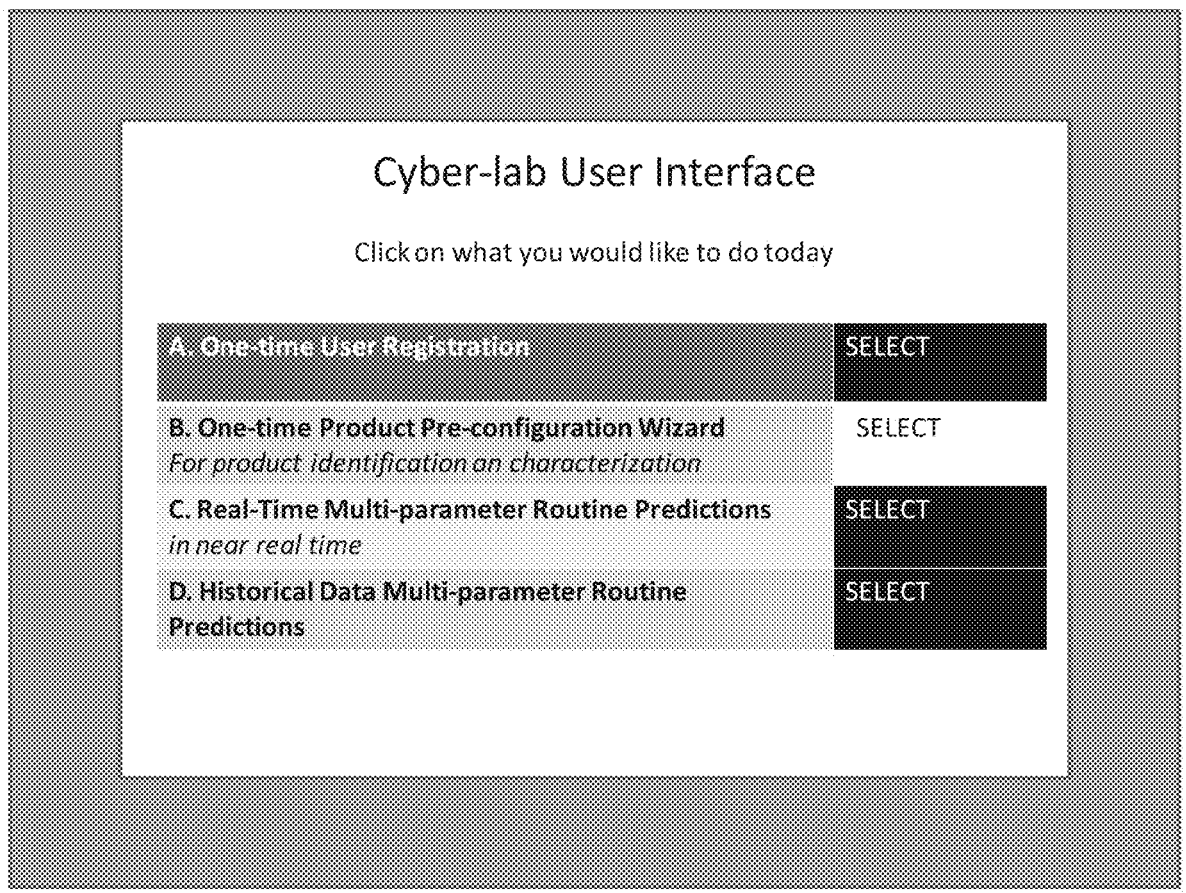
FIG. 25 shows a welcome interface for the online analysis lab.

After logging in to the online analysis lab, the user may be presented with a welcome interface, of which a simple configuration is demonstrated in FIG. 25. The welcome interface may prompt the user to highlight and select, e.g. by cursor selection, key toggles, or touchscreen, one of the available options. In the example depicted, the available options include a One-time User Registration, One-time Product Pre-configuration Wizard, Real-Time Multi-parameter Routine Predictions and Historical Data Multi-parameter Routine Predictions.

Figure 26:
FIG. 26 shows an industry selection interface.

If the user selects the One-time Product Pre-configuration Wizard, the user may be taken to an initial wizard interface as shown in FIG. 26 where the user is prompted to select a particular industry application. The options listed in the interface of FIG. 26 include wine, beer brewing and dairy though any other industrial process may be represented. Furthermore, the product pre-configuration may have categories to enable a user to navigate to the particular industry required. For example, wine, beer brewing and dairy may all be within a higher "food and beverage" category. A search feature may be provided to enable a user to search on the available industries.

Figure 27:
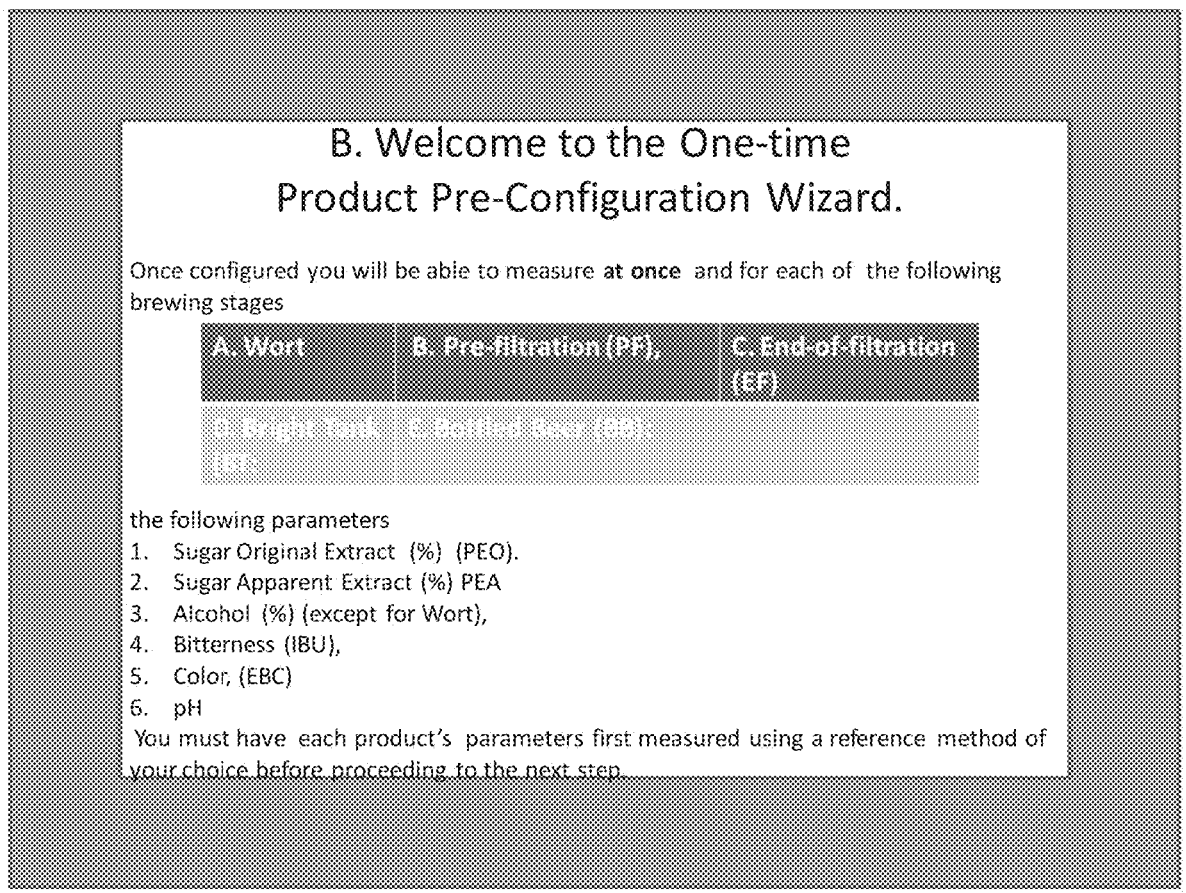
FIG. 27 shows an introductory interface for a pre-configuration wizard.

In the present example, the user selects beer brewing and is taken to the next stage of the pre-configuration wizard, as shown in FIG. 27, which informs the user of the available stages of the brewing process at which the analysis can be performed and the parameters that can be measured.

Figure 28:
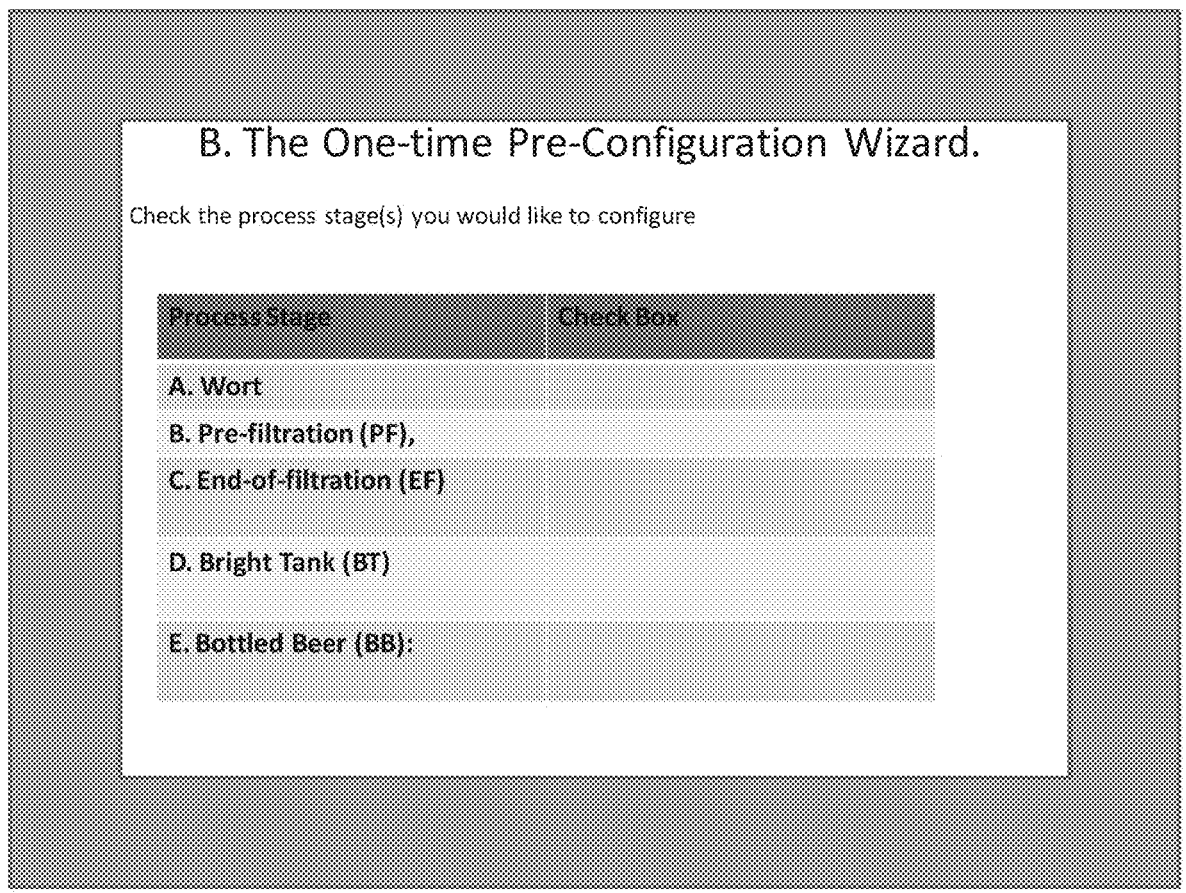
FIG. 28 shows a parameter selection interface for the pre-configuration wizard.

As shown in FIG. 28, the user is then presented with an interface screen that prompts the user to select which of the available processes the user would like to pre-configure. After each selection, the user may be presented with an interface as shown in FIG. 29, which informs and prompts the user for information pertaining to the expected range of results for the given parameter, which in the present example, is the Sugar Original Extract (%) (PEO). Sample ranges may be presented for the information of, and selection by, the user as shown in FIG. 30. The user is able to enter expected ranges for each product's parameters previously determined by the user using any suitable reference method.

The online analysis lab cycles through the screens of FIGS. 28 and 29 until data for each parameter and each process stage has been entered.

If at the welcome screen of FIG. 25, the user selects Real-Time Multi-parameter Routine Predictions, the user is taken to a sampling wizard that guides the user through the process for obtaining and transmitting a sample. The user is prompted to enter samples into the probe sensor which then samples the data and uploads the data to the online analysis laboratory. The user is prompted to enter a file name for the uploaded data so that the data may be stored in associations with the user's account on the online system.

The user can then validate and predict the results for the data. This stage can also be selected through the Historical Data selection of the interface of FIG. 25 by retrieving a previously stored file. FIG. 31 shows a validation screen after execution of the classification process described above. The validation screen indicates whether the range of values for a parameter are within the pre-configured expected ranges. Specific values for the validated parameters can then be predicted by retrieving the appropriate equations for the parameter and using the data and classifications to predict a precise value for the parameter. The final output screen (FIG. 32) may show a summary of the results, including an output range column and a results column which shows the precisely predicted value. The results summary interface can also summarize the user's account credit, provide options for receiving/storing the results and options for further analysis of other samples.

Although the description above contains many specifications, these should not be construed as limiting the scope of the invention but as merely providing illustrations of some of the embodiments of this invention. Thus, the scope of the invention should be determined by the appended claims and their legal equivalents rather than by the examples given.

What is claimed is:

1. A method for analyzing a liquid product comprising:
   (A) obtaining, by a spectroscopic probe sensor, spectroscopic data from the liquid product, wherein the liquid product is an alcoholic beverage;
   (B) transmitting the spectroscopic data from the spectroscopic probe sensor to a data processor;
   (C) receiving a selection by the data processor of one or more parameters of interest for the spectroscopic data, wherein the one or more parameters of interest comprise one or more of pH, sugar content and alcohol content; and
   (D) performing a range determining procedure for at least one parameter of the one or more parameters of interest that determines a range of parameter values for the at least one parameter of interest;
   (E) performing a quantification procedure on the determined range to determine one or more values for the at least one parameter of interest for the determined range;
   (F) wherein the range determining procedure comprises:
      (a) executing a universal calibration model that estimates a first range of parameter values that the spectroscopic data belongs to for the at least one parameter of interest; and
      (b) executing a parameter membership classifier model that a second range of parameter values that the spectroscopic data belongs to for the at least one parameter of interest;
   (G) wherein the quantification procedure comprises:
      (a) retrieving at least one equation for calculating the at least one parameter of interest, wherein the at least one equation is dependent on the determined range for the at least one parameter of interest;
      (b) applying the at least one equation on the spectroscopic data to determine the one or more values for the at least one parameter of interest from the spectroscopic data.

2. The method of claim 1 comprising comparing the first range and the second range.

3. The method of claim 2 wherein if the first range and the second range are equal, determining at least one of the first range or the second range as the range of parameter values for the at least one parameter of interest.

4. The method of claim 2 wherein if the first range and the second range are not equal, filtering the spectroscopic data to remove the spectroscopic data that is outside the first range and the second range and re-executing the universal calibration model and the parameter membership classifier model on the filtered data.

5. The method of claim 4 comprising repeating the steps of executing the universal calibration model, executing the parameter membership classifier model and filtering the spectroscopic data until the first range determined by the universal calibration model is equal to the second range determined by the parameter membership classifier model.

6. The method of claim 1 comprising executing the range determining procedure for each of the one or more parameters of interest.

7. The method of claim 1 comprising transmitting the one or more values for the at least one parameter of interest from the data processor to a user computer device and displaying the one or more values for the at least one parameter of interest on a web-enabled user interface on the user computer device.

8. A system for analyzing a liquid product comprising:
   (A) at least one spectroscopic probe sensor for obtaining spectroscopic data of the liquid product, wherein the liquid product is an alcoholic beverage;
   (B) a data processor programmed to:
      (a) receive the spectroscopic data from the at least one spectroscopic probe sensor and a selection of one or more parameters of interest, wherein the one or more parameters of interest comprise one or more of pH, sugar content and alcohol content; and
      (b) perform a range determining procedure for at least one parameter of the one or more parameters of interest that determines a range of parameter values for the at least one parameter of interest;
      (c) perform a quantification procedure on the determined range to determine one or more values for the at least one parameter of interest for the determined range;
      (d) wherein the range determining procedure comprises:
         (i) executing a universal calibration model that estimates a first range of parameter values that the spectroscopic data belongs to for the at least one parameter of interest; and
         (ii) executing a parameter membership classifier model that determines a second range of parameter values that the spectroscopic data belongs to for the at least one parameter of interest;
      (e) wherein the quantification procedure comprises:
         (i) retrieving at least one equation from a quantification calibration models library for calculating the at least one parameter of interest, wherein the at least one equation is dependent on the determined range for the at least one parameter of interest;
         (ii) applying the retrieved at least one equation for the spectroscopic data to determine the one or more values for the at least one parameter of interest from the spectroscopic data.

9. The system of claim 8 wherein the data processor is programmed to compare the first range and the second range.

10. The system of claim 9 wherein if the first range and the second range are equal then the data processor determines at least one of the first range or the second range as the range of parameter values for the at least one parameter of interest.

11. The system of claim 9 wherein if the first range and the second range are not equal then the data processor is programmed to:
(A) filter the spectroscopic data to remove the spectroscopic data that is outside the first range and the second range; and
(B) re-execute the universal calibration model and the parameter membership classifier model on the filtered data.

12. The system of claim 11 wherein the data processor is configured to repeat the steps of executing the universal calibration model, executing the parameter membership classifier model, and filtering the spectroscopic data until the first range determined by the universal calibration model is equal to the second range determined by the parameter membership classifier model.

13. The system of claim 8 wherein the data processor is programmed to execute the range determining procedure for each of the one or more parameters of interest.

14. The system of claim 8 wherein the at least one spectroscopic probe sensor comprises a light source and a light sensor for detecting light from the liquid product.

15. The system of claim 8 comprising a user computer device that is configured to receive the one or more values for the at least one parameter of interest from the data processor and display the one or more values for the at least one parameter of interest on a web-enabled user interface on the user computer device.

* * * * *